US011186873B2

(12) United States Patent
Jin et al.

(10) Patent No.: US 11,186,873 B2
(45) Date of Patent: Nov. 30, 2021

(54) COMBINATION METHOD FOR TREATING CANCER BY TARGETING IMMUNOGLOBULIN SUPERFAMILY MEMBER 1 (IGSF1) AND MESENCHYMAL-EPITHELIAL TRANSITION FACTOR (MET)

(71) Applicant: WELLMARKER BIO CO., LTD., Seoul (KR)

(72) Inventors: Dong Hoon Jin, Seoul (KR); Seung Woo Hong, Seoul (KR); Jai Hee Moon, Seoul (KR); Jae Sik Shin, Seoul (KR); Seung Mi Kim, Seoul (KR); Dae Hee Lee, Seoul (KR); Eun Young Lee, Seoul (KR); Seul Lee, Seoul (KR)

(73) Assignee: WELLMARKER BIO CO., LTD., Seoul (KR)

( * ) Notice: Subject to any disclaimer, the term of this patent is extended or adjusted under 35 U.S.C. 154(b) by 0 days.

(21) Appl. No.: 15/329,904

(22) PCT Filed: Jul. 29, 2015

(86) PCT No.: PCT/KR2015/007965
§ 371 (c)(1),
(2) Date: Jan. 27, 2017

(87) PCT Pub. No.: WO2016/018088
PCT Pub. Date: Feb. 4, 2016

(65) Prior Publication Data
US 2017/0327894 A1 Nov. 16, 2017

(30) Foreign Application Priority Data
Jul. 29, 2014 (KR) .................. 10-2014-0096636

(51) Int. Cl.
*C12N 15/11* (2006.01)
*C12Q 1/6886* (2018.01)
*C12Q 1/68* (2018.01)
*A61K 31/7088* (2006.01)
*A61K 31/404* (2006.01)
*A61K 31/713* (2006.01)
*C12N 15/113* (2010.01)
*G01N 33/574* (2006.01)

(52) U.S. Cl.
CPC .......... *C12Q 1/6886* (2013.01); *A61K 31/404* (2013.01); *A61K 31/7088* (2013.01); *A61K 31/713* (2013.01); *C12N 15/1138* (2013.01); *C12Q 1/68* (2013.01); *C12Y 207/10001* (2013.01); *G01N 33/574* (2013.01); *G01N 33/57492* (2013.01); *C12N 2310/14* (2013.01); *C12N 2310/141* (2013.01); *C12N 2310/531* (2013.01); *C12N 2320/31* (2013.01); *C12Q 2600/106* (2013.01); *C12Q 2600/158* (2013.01); *G01N 2333/70503* (2013.01)

(58) Field of Classification Search
CPC ............ C12Q 1/6886; C12Q 2600/158; C12N 15/111; C12N 15/113; C12N 2310/14
See application file for complete search history.

(56) References Cited

U.S. PATENT DOCUMENTS

| 2006/0246492 | A1* | 11/2006 | Haber ................. C12Q 1/6886 435/6.14 |
| 2008/0113377 | A1* | 5/2008 | Khvorova ............. C12N 15/111 435/6.11 |
| 2009/0227533 | A1* | 9/2009 | Bader .................. C12N 15/113 514/44 R |
| 2011/0183862 | A1* | 7/2011 | Buendia ............... C12Q 1/6809 506/9 |
| 2011/0201103 | A1* | 8/2011 | Liang ................. C12N 15/1135 435/320.1 |
| 2016/0151406 | A1* | 6/2016 | Bader .................. A61K 31/713 424/450 |

FOREIGN PATENT DOCUMENTS

WO WO-2012059562 A1 * 5/2012 .......... C07K 16/2863

OTHER PUBLICATIONS

Corney et al., Frequent downregulation of miR-34 family in human ovarian cancers, Clinical Cancer Research, vol. 16, pp. 1119-1128. (Year: 2010).*
Dang et al., Underexpression of miR-34a in hepatocellular carcinoma and its constribution towards enhancement of proliferating inhibitory effects of agents targeting c-MET, Plos One, vol. 8, issue 4:e61054, pp. 1-11. (Year: 2013).*
Rimassa et al., Tivantinib: a new promising mesenchymal-epithelial transition factor inhibitor in the treatment of hepatocellular carcinoma, Future Oncology, vol. 9, pp. 153-165. (Year: 2013).*
Patil et al., An integrated data analysis approach to characterize genes highly expressed in hepatocellular carcinoma, Oncogene, vol. 24, pp. 3737-3747. (Year: 2005).*
TargetScanHuman 6.2 predicted targeting of Human IGSF1, Release 6.2, Jun. 2012, accessed and retrieved from www.targetscan.org on Jul. 10, 2018. (Year: 2012).*

(Continued)

*Primary Examiner* — Dana H Shin
(74) *Attorney, Agent, or Firm* — Armstrong Teasdale LLP

(57) ABSTRACT

The present invention relates to a biomarker for predicting susceptibility to an MET inhibitor, and a use thereof, and more specifically, the present invention provides a method for predicting susceptibility to the MET inhibitor. According to the present invention, the present invention has an excellent effect of predicting susceptibility to the MET inhibitor for stomach cancer or lung cancer, and thus the present invention may be usefully employed for treating stomach cancer or lung cancer.

15 Claims, 14 Drawing Sheets
Specification includes a Sequence Listing.

(56) References Cited

OTHER PUBLICATIONS

Suzuki et al., Methylation-associated silencing of microRNA-34b/c in gastric cancer and its involvement in an epigenetic field defect, Carcinogenesis, vol. 31, pp. 2066-2073. (Year: 2010).*

Peng et al., MicroRNA-34A inhibits the growth, invasion and metastasis of gastric cancer by targeting PDGFR and MET expression, Bioscience Reports, vol. 34, pp. 247-256. (Year: 2014).*

Ummanni et al., Prohibitin identified by proteomic analysis of prostate biopsies distinguishes hyperplasia and cancer, Cancer Letters, vol. 266, pp. 171-185. (Year: 2008).*

Chen et al., Profiling and potential tumor markers of pancreatic ductal adnocarcinoma using 2D-DIGE and MALD-TOF-MS: up-regulation of complement C3 and alpha-2HS-glycoprotein, Pancreatology, vol. 13, pp. 290-297. (Year: 2013).*

Chen et al., Identification of prohibitin as a potential biomarker for colorectal carcinoma based on proteomics technology, International Journal of Oncology, vol. 37, pp. 355-365. (Year: 2010).*

Lee et al., Hepatocyte growth factor/c-met signaling in regulating urokinase plasminogen activator in human stomach cancer: A potential therapeutic target for human stomach cancer, The Korean Journal of Internal Medicine, vol. 21, pp. 20-27. (Year: 2006).*

Li et al., miR-34a inhibits migration and invasion by down-regulation of c-Met expression in human hepatocellular carcinoma cells, Cancer Letters, vol. 275, pp. 44-53. (Year: 2009).*

Park et al., Presence of autocrine hepatocyte growth factor-Met signaling and its role in proliferation and migration of SNU-484 gastric cancer cell line, Experimental and Molecular Medicine, vol. 37, pp. 213-219. (Year: 2005).*

"TargetScanHuman 6.2 predicted targeting of Human MET", TargetScanHuman, Human MET 3'UTR, Release 6.2, Jun. 2012, accessed and retrieved from www.targetscan.org on Aug. 14, 2019 (Year: 2012).*

Funakoshi et al., Excessive MET signaling causes acquired resistance and addition to MET inhibitors in the MKN45 gastric cancer cell line, Investigational New Drugs, vol. 31, pp. 1158-1168. (Year: 2013).*

Shin et al., NPS-1034, a novel MET inhibitor, inhibits the activated MET receptor and its constitutively active mutants, Investigational New Drugs, vol. 32, pp. 389-399. (Year: 2014).*

Weinstein-Oppenheimer, et al., "The Raf signal transuction cascade as a target for chemotherapeutic intervention in growth factor-responsive tumors", Pharmacology & Therapeutics 88, 2000, pp. 229-279.

* cited by examiner

COMBINATION METHOD FOR TREATING CANCER BY TARGETING IMMUNOGLOBULIN SUPERFAMILY MEMBER 1 (IGSF1) AND MESENCHYMAL-EPITHELIAL TRANSITION FACTOR (MET)

GOVERNMENT SUPPORT

The present invention was supported by a grant from the National R&D Program for Cancer Control, Ministry of Health & Welfare, Republic of Korea (Grant No. 1420030), under the Research Title "Development of New Therapy and Biomarker for Overcoming Susceptibility to Cetuximab in Patients with Colon Cancer", conducted by Asan Medical Center, Seoul, from May 1, 2014 to Apr. 30, 2017.

Moreover, the present invention was supported by a grant from the Korean Health Technology R&D Project through the Korea Health Industry Development Institute (KHIDI), funded by the Ministry of Health & Welfare, Republic of Korea (Grant number: HI06C0868), under the Research Title "Development of Innovative Anticancer Agents Targeting Receptor Tyrosine Kinase (RTK)", conducted by Institute for Innovative Cancer Research, Asan Medical Center, Seoul, from Dec. 1, 2011 to Nov. 30, 2016.

RELATED APPLICATIONS

This application is a United States National Phase entry of International Application No. PCT/KR2015/007965 filed Jul. 29, 2015, which claims the benefit of Korean Patent Application No. 10-2014-0096636 filed Jul. 29, 2014. The entire contents of both of the foregoing applications are hereby incorporated by reference herein.

TECHNICAL FIELD

The present invention relates to a novel biomarker for predicting susceptibility to an MET inhibitor, and a use thereof.

BACKGROUND ART

Generally, in anticancer therapies, the response of the body to an anticancer drug administered is highly dependent on susceptibility to the drug of cancer cells targeted by the drug. The susceptibility of cancer cells to the drug differs greatly in cancer cells. This difference in susceptibility is caused by quantitative or qualitative differences in target molecules of the drug or related factors, acquisition of drug resistance, etc. Based on this background, if the genetic changes of cancer cells that specifically occur when the targeted cancer cells are sensitive to a drug are known, it is possible to determine the efficacy of the drug early in its development, establish treatment methods, and select a new treatment method, which are very useful. Moreover, after drug treatment in cancer cells isolated from a cancer tissue obtained by the biopsy prior to the treatment, if it is determined by the above-mentioned changes whether these cancer cells are sensitive to the drug, it is possible to predict whether the drug treatment is effective, which is clinically useful.

That is, this anticancer drug differs among individuals in tolerance and toxicity and tends to be resistant to more than half of the same patients, and thus the screening using an appropriate treatment response marker can lead to a revolutionary advance in treatment with anticancer drugs.

Accordingly, studies on treatment response of each anticancer agent to a specific gene have continued to progress.

However, due to the complex action of biological response-related factors, the diversity of therapeutic agents and administration routes, and the difficulty of obtaining a large number of samples, the results are not so satisfactory.

Meanwhile, one of the major mechanisms of cell regulation is the sequential regulation of biochemical pathways in cells for extracellular signaling. Protein phosphorylation refers to the intracellular signaling between molecules, ultimately leading to cellular reactions. These signaling cascades are highly regulated and often redundant as evidenced by the presence of several protein kinases as well as phosphatase. Phosphorylation is a process that occurs in all cells, and the phenotype of a cell is significantly influenced by the activity of this pathway. Thus, at present, the majority of disease states and/or diseases are believed to be caused by abnormal activity or functional mutations of molecular components in kinase cascades (Weinstein-Oppenheimer et al. Pharma. &. Therap., 2000, 88, 229-279).

Among other, MET (c-MET) is a representative receptor tyrosine kinase (RTK) that exists on the surface of cells and is overexpressed in many types of cancers, and in most cases, patients with overexpression of MET have a poor prognosis.

This MET signaling in cancer can be activated in two ways: MET activation is mediated (i) by an HGF-dependent mechanism by binding to its ligand hepatocyte growth factor (HGF) to promote intracellular signaling; or (ii) by an HGF-independent mechanism such as amplification of the MET gene or mutation of the MET gene.

However, most of the inhibitors developed for MET are focused on the MET activation by the HGF-dependent mechanism, and treatment methods using a biomarker for a disease such as cancer caused by the MET activation mediated by the HGF-independent mechanism are not known at present.

DISCLOSURE

Technical Problem

Under these circumstances, the present inventors have made extensive efforts to develop biomarkers capable of predicting susceptibility to an MET inhibitor in cancers due to MET activity mediated by an HGF-independent mechanism. As a result, we have analyzed the expression pattern of IGSF1 as a biomarker for predicting susceptibility to an MET inhibitor in gastric cancer and lung cancer and the expression pattern of MET gene and/or its protein and found that the inhibition of IGSF1 and MET genes in gastric cancer and lung cancer cell lines significantly decreased the survival, invasion and migration of cancer cells, thereby completing the present invention.

Accordingly, an object of the present invention is to provide a biomarker for predicting susceptibility to an MET inhibitor.

Another object of the present invention is to provide a composition for predicting susceptibility to an MET inhibitor.

Still another object of the present invention is to provide a kit for predicting susceptibility to an MET inhibitor.

Yet another object of the present invention is to provide an enhancer for enhancing susceptibility to an MET inhibitor.

Still yet another object of the present invention is to provide a method for predicting susceptibility to an MET inhibitor.

A further another object of the present invention is to provide a method for enhancing susceptibility to an MET inhibitor.

Another further object of the present invention is to provide a pharmaceutical composition for preventing or treating a disease associated with dysregulation of MET signaling pathway.

Hereinafter, the present invention will be described in more detail.

According to one aspect of the present invention, there is provided a biomarker for predicting susceptibility to a MET inhibitor, comprising immunoglobulin superfamily member 1 (IGSF1) gene (NM_001555.2).

The most significant feature of the present invention is to predict susceptibility to an MET inhibitor using an IGSF1 gene and its product protein as biomarkers.

The biomarker of the present invention can be used as an indicator of susceptibility to an anticancer agent as the MET inhibitor, has excellent accuracy and reliability as a susceptibility marker to an anticancer agent, and thus can be used for the treatment of occurrence, development, and/or invasion of cancer.

As used herein, the term "susceptibility" refers to whether a particular drug has an effect on cancer in an individual patient.

For example, the specific drug is mainly an anticancer agent, and the anticancer agent may have an effect depending on the type of cancer or not. Moreover, it is known that, even in the case of cancer recognized as being effective, the anticancer drug has an effect depending on individual patients or not. Whether or not an anticancer drug has an effect on cancer in an individual patient is referred to as anticancer drug susceptibility. Therefore, if it is possible to predict a patient from which the effect can be predicted (responder) prior to the initiation of treatment and a patient from which the effect cannot be predicted (non-responder), a chemotherapy with high efficacy and safety can be realized.

As used herein, the term "prediction" is used to refer to the ability of a subject patient to respond favorably or adversely to a drug or set of drugs. In one embodiment, the prediction is about the degree of the response. For example, the prediction may be associated with whether a patient will survive without cancer recurrence after treatment with a particular therapeutic agent and/or after surgical removal of primary tumor and/or after chemotherapy for a predetermined period and/or the likelihood of the survival. The prediction of the present invention can be used clinically to determine the treatment strategy by selecting the most appropriate treatment regimen for colon cancer patients. The prediction of the present invention is a useful tool for predicting whether a patient will respond favorably to a given therapeutic treatment, for example, to administration of a given therapeutic agent or combination, surgical intervention, chemotherapy, etc. or whether a patient will survive for a long time after a therapeutic treatment.

Moreover, according to a preferred embodiment of the present invention, the MET is activated in a hepatocyte growth factor (HGF)-independent manner.

MET activation is mediated by an HGF-dependent mechanism by binding to its ligand hepatocyte growth factor (HGF) to promote intracellular signaling; or by an HGF-independent mechanism such as amplification of the MET gene or mutation of the MET gene. The MET of the present invention is activated in an HGF-independent manner, and the HGF gene and/or its product protein is not expressed or under-expressed.

Moreover, according to a preferred embodiment of the present invention, the activation is phosphorylation of MET induced by co-expression of immunoglobulin superfamily member 1 (IGSF1) gene and mesenchymal-epithelial transition factor (MET) gene (NM_001127500.1).

Therefore, according to the present invention, the marker of the present invention predicts susceptibility to an MET inhibitor when MET is activated in an HGF-independent manner, and can be applied when a desired effect is not obtained in cancer cells with high expression of HGF.

That is, the biomarker of the present invention targets cancer cells or a subject with cancer in which the HGF gene and/or its product protein is not expressed or under-expressed to confirm the expression level of a gene in cells.

According to another aspect of the present invention, there is provided a composition for predicting susceptibility to an MET inhibitor, comprising an agent for measuring the expression level of immunoglobulin superfamily member 1 (IGSF1) gene (NM_001555.2) or the expression level of its protein.

According to a preferred embodiment of the present invention, the MET of the present invention is activated in an HGF-independent manner, and the HGF gene and/or its product protein is not expressed or under-expressed.

Moreover, according to a preferred embodiment of the present invention, the activation is phosphorylation of MET induced by co-expression of immunoglobulin superfamily member 1 (IGSF1) gene and mesenchymal-epithelial transition factor (MET) gene (NM_001127500.1).

Therefore, according to the present invention, the composition of the present invention predicts susceptibility to an MET inhibitor when MET is activated in an HGF-independent manner, and can be applied when a desired effect is not obtained in cancer cells with high expression of HGF.

Furthermore, according to a preferred embodiment of the present invention, the MET inhibitor is a therapeutic agent for treating at least one selected from the group consisting of adrenocorticotropic hormone (ACTH)-producing tumor, acute lymphocytic leukemia or acute lymphoblastic leukemia, acute or chronic lymphocytic leukemia, acute non-lymphocytic leukemia, bladder cancer, brain tumor, breast cancer, cervix cancer, chronic myelogenous leukemia, lymphoma, endometriosis, esophageal cancer, Ewing's sarcoma, tongue cancer, Hodgkin's lymphoma, Kaposi's sarcoma, kidney cancer, liver cancer, lung cancer, mesothelioma, multiple myeloma, neuroblastoma, non-Hodgkin's lymphoma, osteosarcoma, ovarian cancer, mammary cancer, prostate cancer, pancreatic cancer, colon cancer, penile cancer, retinoblastoma, skin cancer, gastric cancer, thyroid cancer, uterine cancer, testicular cancer, Wilm's tumor, and trophoblastoma. More preferred is ACTH-producing tumor, acute lymphocytic leukemia or acute lymphoblastic leukemia, acute or chronic lymphocytic leukemia, acute non-lymphocytic leukemia, bladder cancer, brain tumor, breast cancer, cervix cancer, chronic myelogenous leukemia, bowel cancer, T-zone lymphoma, endometriosis, esophageal cancer, gall bladder cancer, Ewing's sarcoma, tongue cancer, Hodgkin's lymphoma, Kaposi's sarcoma, kidney cancer, liver cancer, lung cancer, mesothelioma, multiple myeloma, neuroblastoma, non-Hodgkin's lymphoma, osteosarcoma, ovarian cancer, mammary cancer, prostate cancer, pancreatic cancer, colorectal cancer, penile cancer, retinoblastoma, skin cancer, gastric cancer, thyroid cancer, uterine cancer, testicular cancer, Wilm's tumor, or trophoblastoma, and the most preferred is lung cancer or gastric cancer.

In the present invention, the MET inhibitor refers to an anticancer agent. Any MET inhibitor may be used as long as it has an anticancer effect and preferably comprises at least one selected from the group consisting of anti-MET antibodies, decoy MET receptors, MET peptide antagonists, dominant negative MET mutations, MET-specific antisense oligonucleotides and ribozymes, and selective small molecule MET kinase inhibitors.

Unless otherwise specified herein, the term "expression level of a gene or expression level of its protein" as used herein refers to the detection of an object to be detected in a sample of interest. In the present invention, the object to be detected is an mRNA and/or protein of a corresponding gene in the sample. That is, the gene expression can be determined by detecting RNA as a transcription product of the gene or a protein as a gene product.

The detection of RNA or protein can be carried out by extracting an RNA or protein from a sample and detecting the RNA or protein in the extract. The detection of the RNA or protein can be measured by an immunoassay method, a hybridization reaction, and an amplification reaction, but is not limited thereto, and can be easily carried out using various techniques known in the art.

Moreover, according to a preferred embodiment of the present invention, the agent for measuring the gene expression level comprises an antisense oligonucleotide, a primer pair or a probe that specifically binds to the mRNA of the gene.

The agent for measuring the expression of mRNA is selected from the group consisting of an antisense oligonucleotide, a primer pair, a probe, and combinations thereof that are specific to the gene. That is, the detection of nucleic acid can be performed by an amplification reaction using a nucleic acid molecule encoding the gene or one or more oligonucleotide primers hybridized to a complement of the nucleic acid molecule.

For example, the detection of mRNA using a primer can be performed by amplifying the gene sequence using an amplification method such as PCR and then determining the amplification of the gene by a method known in the art.

Moreover, according to a preferred embodiment of the present invention, the agent for measuring the expression level of a protein comprises an antibody, a peptide or a nucleotide that specifically binds to the protein.

The agent for measuring the expression level of a protein refers to an antibody that specifically binds to the protein and comprises polyclonal antibodies, monoclonal antibodies, recombinant antibodies, and combinations thereof.

The antibodies comprises polyclonal antibodies, monoclonal antibodies, recombinant antibodies, and intact antibodies having two full length light chains and two full length heavy chains as well as functional fragments of antibody molecules such as Fab, F(ab'), F(ab')2, and Fv. The antibodies can be easily produced by any technique well known in the art to which the present invention pertains, and commercially produced antibodies are also available.

The composition of the present invention may further comprise a label enabling quantitative or qualitative measurement of the formation of an antigen-antibody complex, a conventional tool, a reagent, etc. that are used for immunological analysis, in addition to the above-described agent for measuring the gene expression.

Examples of labels enabling quantitative or qualitative measurement of the formation of an antigen-antibody complex include, but not limited to, enzymes, fluorescent substances, ligands, luminescent substances, microparticles, redox molecules and radioactive isotopes. Examples of enzymes that can be used as detection labels include, but not limited to, β-glucuronidase, β-D-glucosidase, β-D-galactosidase, urease, peroxidase, alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphoenolpyruvate decarboxylase, β-lactamase, etc. Examples of fluorescent substances include, but not limited to, fluorescein, isothiocyanate, rhodamine, phycoerythrin, phycocyanin, allophycocyanin, o-phthaldehyde, fluorescamine, etc. Examples of ligands include, but are not limited to, biotin derivatives, etc. Examples of luminescent substances include, but not limited to, acridinium esters, luciferin, luciferase, etc. Examples of microparticles include, but not limited to, colloidal gold, colored latex, etc. Examples of redox molecules include, but not limited to, ferrocene, ruthenium complexes, viologen, quinone, Ti ions, Cs ions, diimide, 1,4-benzoquinone, hydroquinone, K4W $(CN)^8$, $[Os(bpy)_3]^{2+}$, $[RU(bpy)_3]^{2+}$, $[MO\ CN)_8]^{4-}$, etc. Examples of radioactive isotopes include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, etc.

Examples of the tool or reagent include, but are not limited to, suitable carriers, solubilizers, detergents, buffers, stabilizers, etc. When the labeling substance is an enzyme, it may include a substrate capable of measuring the enzyme activity and a reaction terminator. Examples of carriers include soluble carriers and insoluble carriers. Examples of soluble carriers include physiologically acceptable buffers known in the art, for example PBS, and examples of insoluble carriers include polystyrene, polyethylene, polypropylene, polyester, polyacrylonitrile, fluorocarbon resin, crosslinked dextran, polysaccharide, other papers, glasses, metals, agarose, and combinations thereof.

The composition of the present invention includes the above-described biomarker as an active ingredient, and thus a description thereof will be omitted to avoid excessive complexity of the specification.

According to still another aspect of the present invention, there is provided a kit for predicting susceptibility to an MET inhibitor, comprising the above-described composition.

The kit may include a tool, a reagent, etc., which are commonly used in the art for immunological analysis, in addition to the above-described agent for measuring the expression level of a gene or the expression level of its protein.

Examples of the tool or reagent include, but are not limited to, suitable carriers, labeling substances capable of generating a detectable signal, chromophores, solubilizers, detergents, buffers, stabilizers, etc. When the labeling substance is an enzyme, it may include a substrate capable of measuring the enzyme activity and a reaction terminator. Examples of carriers include soluble carriers and insoluble carriers. Examples of soluble carriers include physiologically acceptable buffers known in the art, for example PBS, and examples of insoluble carriers include polystyrene, polyethylene, polypropylene, polyester, polyacrylonitrile, fluorocarbon resin, crosslinked dextran, polysaccharide, polymers such as magnetic microparticles composed of latex plated with metals, other papers, glasses, metals, agarose, and combinations thereof.

The kit of the present invention includes the above-described biomarker and composition, and thus a description thereof will be omitted to avoid excessive complexity of the specification.

According to yet another aspect of the present invention, there is provided an enhancer or composition for enhancing susceptibility of a subject to an mesenchymal-epithelial transition factor (MET) inhibitor, comprising an inhibitor for inhibiting the expression of immunoglobulin superfamily member 1 (IGSF1) gene (NM_001555.2) or the expression or activity of its protein as an active ingredient.

According to a preferred embodiment of the present invention, the enhancer or composition for enhancing susceptibility further comprises an inhibitor for inhibiting the expression of mesenchymal-epithelial transition factor (MET) gene (NM_001127500.1) or the expression or activity of its protein.

In the present invention, the subject enhances susceptibility to an MET inhibitor when MET is activated (phosphorylated) in a hepatocyte growth factor (HGF)-independent manner, and can be applied when a desired effect is not obtained in cancer cells activated (phosphorylated) in an HGF-independent manner.

That is, the inhibitor of the present invention for inhibiting the expression of IGSF1 and/or MET gene(s) or the expression or activity of its protein can reduce the phosphorylation of MET and reduce the migration and invasion of cancer cells, thereby exhibiting an excellent anticancer effect.

Moreover, according to a preferred embodiment of the present invention, the inhibitor comprises at least one selected from the group consisting of small interfering RNA (siRNA), short hairpin RNA (shRNA), microRNA (miRNA), ribozyme, DNAzyme, peptide nucleic acids (PNAs), antisense oligonucleotides, antibodies, aptamers, natural extracts, and chemicals. More preferred is antisense oligonucleotides, aptamers, small interfering RNA (siRNA), short hairpin RNA (shRNA), or microRNA (miRNA) that specifically bind to mRNA of the gene, and the most preferred is small interfering RNA (siRNA), short hairpin RNA (shRNA), or microRNA (miRNA).

As used herein, the term "microRNA (miRNA)" refers to approximately 22-nt non-translated RNA that acts as a post-translational inhibitor through base-pairing with the 3' untranslated region (UTR) of mRNA. The method for producing miRNA is not particularly limited, and methods known in the art can be used.

According to a preferred embodiment of the present invention, the microRNA (miRNA) is miR-34a comprising the nucleotide sequence of SEQ ID NO: 1 or miR-34c comprising the nucleotide sequence of SEQ ID NO: 2.

As used herein, the term "siRNA" refers to small RNA fragments of 21-25 nucleotides in length that are produced by cleavage of a double-stranded RNA by dicer and specifically bind to an mRNA having a complementary sequence to inhibit the expression. That is, it refers to the inhibition of the gene expression by specifically binding to a target mRNA of the present invention. The siRNA can be chemically or enzymatically synthesized. The method for producing siRNA is not particularly limited, and methods known in the art can be used.

As used herein, the term "shRNA" refers to a single stranded RNA consisting of 45 to 70 nucleotides in length and means that oligo DNA connecting 3-10 base linkers are synthesized between the sense and complementary nonsense of target gene siRNA sequences and then cloned to plasmid vector, or shRNA is inserted and expressed into retrovirus such as lentivirus and adenovirus to thereby make shRNA of hairpin structure with loop, which is converted into siRNA by dicer in cells, thus exhibiting RNAi effects. Expression constructs/vectors containing small hairpin RNA (shRNA) can be produced by methods known in the art.

According to a preferred embodiment of the present invention, the small interfering RNA (siRNA) is IGSF1 siRNA comprising the nucleotide sequence of SEQ ID NO: 3, IGSF1 siRNA comprising the nucleotide sequence of SEQ ID NO: 4 or MET siRNA comprising the nucleotide sequence of SEQ ID NO: 5, and the short hairpin RNA (shRNA) is IGSF1 shRNA comprising the nucleotide sequence of SEQ ID NO: 6 or MET shRNA comprising the nucleotide sequence of SEQ ID NO: 7.

According to the present invention, when the expression of IGSF1 gene or its product protein in cancer cells is inhibited by the RNAi method (siRNA, shRNA, and microRNA), the phosphorylation of MET is reduced in a siRNA concentration-dependent manner.

Furthermore, in the present invention, the cancer cells in which the expression of IGSF1 and/or MET gene(s) or its product protein is inhibited show significantly low survival rate, migration and invasion as compared with cancer cells in which the expression is maintained.

Therefore, this suggests that the inhibition of the expression of IGSF1 and/or MET gene(s) or the expression or activity of its protein enhances the susceptibility of cancer cells to an MET inhibitor, and based on this, the present invention has an excellent effect of enhancing susceptibility of a subject to an MET inhibitor.

The enhancer or composition for enhancing susceptibility of the present invention may further comprise a pharmaceutically acceptable carrier. Examples of pharmaceutically acceptable carriers that can be used in the present invention may be selected from conventional excipients, disintegrants, binders, lubricants and other additives such as stabilizers, emollients, emulsifiers, etc. Examples of excipients may include microcrystalline cellulose, lactose, low-substituted hydroxy cellulose, etc. and examples of disintegrants may include sodium starch glycolate, calcium monohydrogen phosphate anhydrous, etc. Examples of binders may include polyvinylpyrrolidone, low-substituted hydroxypropyl cellulose, etc., and examples of lubricants may be selected from magnesium stearate, silicon dioxide, talc, etc.

The composition of the present invention enhances the susceptibility to the MET inhibitor using the expression level of the above-described biomarker, and thus a description thereof will be omitted to avoid excessive complexity of the specification.

According to a further aspect of the present invention, there is provided a pharmaceutical composition for preventing or treating a disease associated with dysregulation of MET signaling pathway, comprising the above-described enhancer for enhancing susceptibility and an MET inhibitor as active ingredients.

In the present invention, examples of diseases associated with the dysregulation of the MET signal transduction pathway include cancers, atherosclerosis, pulmonary fibrosis, renal fibrosis and regeneration, liver diseases, allergic diseases, inflammatory diseases, autoimmune diseases, cerebrovascular diseases, or symptoms associated with organ transplantation, preferably cancers.

That is, the inhibitor for inhibiting the expression of IGSF1 and/or MET gene(s) or the expression or activity of its protein as the enhancer for enhancing susceptibility to an MET inhibitor of the present invention increases the susceptibility to an anticancer agent and, upon administration with the anticancer drug, increases the efficacy of the anticancer drug, thereby facilitating the treatment of cancers.

The "cancer" to be improved, prevented or treated by the composition of the present invention is a generic term for diseases caused by cells with aggressive properties of cells that divide and grow beyond the normal limits, invasive properties of cells that invade the surrounding tissue, and metastatic properties of cells that spread to other areas of the body. In the present specification, the term "cancer" is also used to refer to a malignant tumor.

Examples of cancers to which the composition of the present invention may be applied include, but not limited to, breast cancer, lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, small intestine cancer, endocrine cancer, endocrine cancer, parathyroid cancer, adrenal cancer, soft tissue tumor, urethral cancer, prostate cancer, bronchogenic cancer, bone marrow tumor, etc.

Preferably, the composition of the present invention can be used for the treatment or prevention of gastric cancer or lung cancer.

As used herein, the term "prevention" refers to the inhibition of the occurrence of a disease or disorder in an animal that may be predisposed to the disease or disorder, but has not yet been diagnosed as having it. As used herein, the term "treatment" refers to: (i) the inhibition of the development of a disease or disorder; (ii) the relief of a disease or disorder; and (iii) the elimination of a disease or disorder.

The pharmaceutical composition of the present invention may further comprise a pharmaceutically acceptable carrier.

The pharmaceutically acceptable carrier included the pharmaceutical compositions of this invention is commonly used for formulation, and examples thereof include, but not limited to, lactose, dextrose, sucrose, sorbitol, mannitol, starch, acacia rubber, potassium phosphate, arginate, gelatin, potassium silicate, microcrystalline cellulose, polyvinylpyrrolidone, cellulose, water, syrups, methyl cellulose, methyl hydroxybenzoate, propyl hydroxybenzoate, talc, magnesium stearate, and mineral oils. The pharmaceutical composition of the present invention may further include a lubricant, a humectant, a sweetener, a flavoring agent, an emulsifier, a suspending agent, and a preservative, in addition to the above-described components. Details of suitable pharmaceutically acceptable carriers and formulations can be found in Remington's Pharmaceutical Sciences (19th ed., 1995).

A suitable dose of the pharmaceutical composition of the present invention may vary depending various factors such as formulation methods, administration ways, a patient's age, body weight, sex, severity of disease, and diet, administration time, administration route, excretion rate and response.

Meanwhile, the pharmaceutical composition of the present invention is administered at a daily dose of 0.0001 to 100 mg/kg (body weight).

The pharmaceutical composition of the present invention may be administered orally or parenterally. For parenteral administration, the pharmaceutical composition of the present composition may be administered by intravenous, subcutaneous, intramuscular, intraperitoneal, and intradermal routes. The administration route of the pharmaceutical composition of the present invention may be preferably determined depending on the type of disease.

The concentration of the inhibitor for inhibiting the expression of a gene of interest or its protein in the enhancer contained in the composition of the present invention as an active ingredient is determined depending on the purpose of the treatment, the patient's condition, the period required, and the severity of disease, but is not limited to a specific range.

The pharmaceutical composition of the present invention may be formulated with a pharmaceutically acceptable carrier and/or excipient in a unit dose form or in a multi-dose form according to any method that is well known to those skilled in the art. The formulation may be in the form of a solution, a suspension or an emulsion in oil or aqueous medium, or extracts, powders, granules, tablets, or capsules, and may further comprise a dispersant or a stabilizer.

The composition of the present invention enhances the cell death of cancer cells using the above-described enhancer for enhancing susceptibility and an MET inhibitor that is an anticancer agent, and thus a description thereof will be omitted to avoid excessive complexity of the specification.

According to another further aspect of the present invention, there is provided a method for predicting susceptibility to an MET inhibitor, comprising the steps of: (a) preparing a biological sample from a subject; and (b) measuring the expression level of immunoglobulin superfamily member 1 (IGSF1) gene (NM_001555.2) or the expression of its protein in the biological sample, wherein in step (b), if the expression level of IGSF1 gene or the expression level of its protein is higher than a control group, it is determined that the subject is sensitive to the MET inhibitor.

Unless otherwise specified herein, the term "control group" refers to the expression level of a gene of interest or its protein in a normal healthy person or the expression level of a gene of interest or its protein in a patient to be compared.

The prediction method of the present invention comprises obtaining a biological sample from a subject patient, measuring the expression of IGSF1 in the sample, and if the expression of a gene of interest is increased compared to a control sample, determining that the sample of interest is sensitive to an MET inhibitor.

Moreover, according to a preferred embodiment of the present invention, the subject is one in which the HGF gene or its protein is under-expressed or not expressed compared to a control group.

Furthermore, according to a preferred embodiment of the present invention, the subject is one in which the MET gene or its protein is highly-expressed compared to a control group.

More specifically, if it is determined that the HGF gene or its protein is under-expressed or not expressed compared to a control group and that the expression levels of the IGSF1 and MET genes or their proteins are found to be increased compared to the values of the control, it is determined that the tumor cells of interest obtained from a subject patient are sensitive to the MET inhibitor that is an anticancer agent.

That is, when the IGSF1 gene or its protein is highly-expressed in a patient in which the HGF is not expressed or under-expressed, the IGSF1 gene induces the activation of MET, and thus it is determined that the IGSF1 gene is sensitive to the MET inhibitor.

The term "under-expression" used herein to refer to the expression levels of genes refers to the value or level of a biomarker in a biological sample that is lower than the value or level of a biomarker detected in a biological sample obtained from a healthy or normal individual or an individual to be compared, when the biomarker exhibits or indicates an abnormal process, a disease or other conditions in the individual.

The term "high-expression" used herein to refer to the expression levels of the genes refers to the value or level of a biomarker in a biological sample that is higher than the value or level of a biomarker detected in a biological sample obtained from a healthy or normal individual or an individual to be compared, when the biomarker exhibits or indicates an abnormal process, a disease or other conditions in the individual.

Moreover, the terms used to refer to the expression levels of genes may be referred to those having a "differential level" or "differential level" or those differentially expressed compared to the "normal" expression level of the biomarker and encompass both qualitative and quantitative differences in expression.

As used herein, the term "biological sample" refers to any sample obtained from an individual from which the biomarker of the present invention can be detected.

According to a preferred embodiment of the present invention, the biological sample is any one selected from the group consisting of saliva, biopsy, blood, skin tissue, liquid culture, feces and urine, but not limited thereto, and can be prepared by any method that is commonly used in the art.

The method of the present invention determines the susceptibility using the above-described biomarker, and thus a description thereof will be omitted to avoid excessive complexity of the specification.

According to still another further aspect of the present invention, there is provided a method for enhancing susceptibility to an MET inhibitor, comprising co-administering to a subject the above-described enhancer for enhancing susceptibility and an MET inhibitor.

The method of the present invention enhances the susceptibility using the above-described enhancer for enhancing susceptibility and the MET inhibitor that is an anticancer agent, and thus a description thereof will be omitted to avoid excessive complexity of the specification.

Advantageous Effects

With the use of the biomarker for predicting susceptibility to the MET inhibitor of the present invention, it is possible to reliably determine the susceptibility of individual patients prior to the initiation of treatment, and thus it is possible to select an anticancer agent having a high therapeutic effect. Moreover, it is possible to avoid the use of an anticancer agent that has no effect, and thus it is possible to avoid unnecessary side effects.

Figures 1A, 1B:
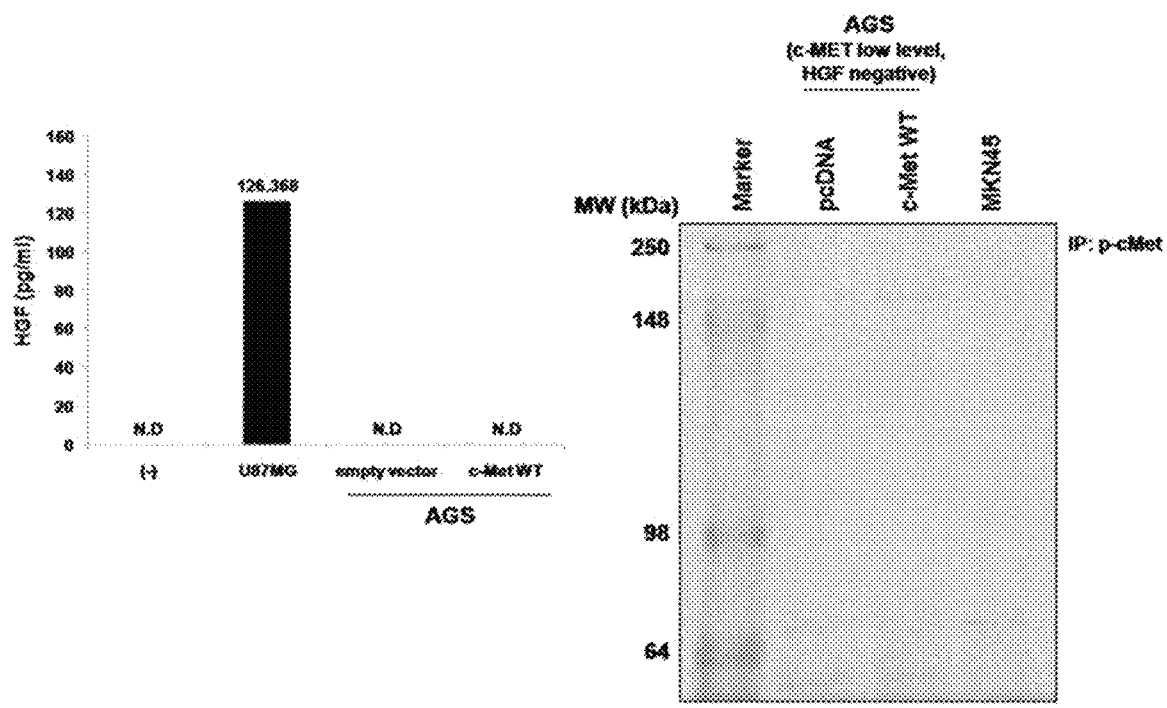
FIG. 1A shows the identification of a marker for the induction of HGF-independent MET phosphorylation. The left panel is a graph showing the HGF-independent MET phosphorylation induced by overexpressing the MET wild-type DNA in HGF-negative human gastric cancer cell line AGS. The right panel is a blot assay showing the results of silver staining performed to identify the protein binding to MET after immunoprecipitation using p-MET antibody.
FIG. 1B shows the results of the MALDI-TOF analysis for the identification of immunoglobulin superfamily member 1 (IGSF1) as a marker for the induction of HGF-independent MET phosphorylation.

Hereinafter, the following Examples are provided to illustrate the present invention in more detail, and it will be apparent to those skilled in the art to which the present invention pertains that the scope of the present invention is not limited to these Examples and various changes can be made without departing from the give of the preset invention.

Experimental Method and Conditions

Induction of HGF-Independent MET Phosphorylation

HGF-independent human gastric cancer AGS cell lines were transfected with MET wild-type plasmid for 48 hours, and then the cell culture media were collected and analyzed by HGF ELISA assay (R&D Systems, Inc, Minneapolis, Minn., USA). Cell lysates were collected, and the changes in MET and IGSF1 proteins were verified by Western blot analysis.

Immunoprecipitation and MALDI-TOF

To identify the genes involved in HGF-independent MET activation, the MET wild-type plasmid was overexpressed in human gastric cancer cell line AGS for 48 hours, and then cell lysates were collected. 500 µg of human gastric cancer cell lysates were mixed with 1 µg of anti-pMET antibody, and then cultured at 4° C. for 12 hours. Then, 20 µl of Protein-Sepharose beads (Santa Cruz Biotechnology, Santa Cruz, Calif., USA) were added, and the mixture was further reacted for 2 hours. Immunoprecipitates were washed with a buffer (Nondiet P-40 lysis buffer) five times, and 20 µl of 2× SDS sample buffer was added and heated. The immunoprecipitates were subjected to SDS-PAGE and stained with silver staining kit (GE Healthcare Bio-Sciences Corp. NJ, USA). Proteins identified by silver staining were identified through mass spectrometry to identify the proteins involved in HGF-independent MET activation.

Western Blot Analysis

To perform Western blot analysis, proteins isolated from the respective cells were separated by SDS-PAGE and transferred to membranes (PolyScreen membranes; New England Nuclear, Boston, Mass., USA). The proteins were incubated with various antibodies (anti-phospho MET, E-cadherin (Cell signaling Technology, Beverly, Mass., USA), anti-MET, anti-r-tubulin (Santa Cruz Biotechnology, Santa Cruz, Calif., USA), anti-IGSF1 (Abnova, Jhouzih, Taipei, Taiwan)) at 4° C. for 12 hours and then washed with 1× TBS-T buffer three times for 10 minutes. The proteins were incubated with appropriate anti-rabbit-HRP or anti-mouse-HRP secondary antibody at room temperature for 2 hours and washed with 1× TBS-T buffer three times for 10 minutes, and then the expression of the proteins was detected using ECL solution (GE Healthcare Bio-Sciences Corp.).

Invasion Chamber Assay and Cell Migration Assay

HGF-independent human gastric cancer cell lines MKN45 and SNU638 and lung cancer cell line HCC827 were transfected with IGSF1 siRNA or MET siRNA for 48 hours. Plate inserts (BD Biosciences) of 8 mm pore size were placed in a 24-well plate, and each 100 µl of matrigel (BD Biosciences) was seeded on each at a concentration of 200 µg/ml and incubated in a $CO_2$ incubator for 30 minutes. $2.5 \times 10^4$ cells transfected with MET or IGSF1 siRNA were placed in the insert plate in a total volume of 100 µl in serum-free media. 400 µl of growth media (RPMI1640+10% FBS) were seeded on the bottom plate and cultured in a $CO_2$ incubator for 24 hours. After 24 hours, the insert plate was washed with PBS, and the remaining cells were wiped with a cotton swab and fixed in 10% formalin for 20 minutes.

After washing with purified water, the cells were stained with 0.01% crystal violet solution for 20 minutes and washed with warm water, and then the number of migrated cells was counted. In the case of the migration assay, the same procedure as above was carried out without coating the insert plate. The number of cells migrated through the insert plate in the control and the gastric cancer and lung cancer cell lines transfected with MET or IGSF1 siRNA was counted and verified.

Inhibition of Gene Expression

Production of siRNA and shRNA

HGF-independent human gastric cell lines MKN45 and SNU638 and lung cancer cell line HCC827 were transfected with IGSF1 siRNA (SEQ ID NO: 3 IGSF1 #1; 5'-GCAG-GUCUUUACCGGUGCU-3', SEQ ID NO: 4 IGSF1 #2; 5'-GGUGCUGCUACUGGAAGGA-3'), MET siRNA (SEQ ID NO: 5; 5'-AAAGATAAACCTCTCATAATG-3'), IGSF1 shRNA (SEQ ID NO: 6; 5'-CAAAGAUG-GAAGUGAAAUA UCUCUAUUUCACUUCCAUCUUU-GUU-3') and/or MET shRNA (SEQ ID NO: 7; 5'-GCCAGC-CUGAAUGAUGACAUCUCUGUCAUCAUUCAGGCU GGCUU-3') for 48 hours, and cell lysates were collected and the changes in MET and IGSF1 proteins were verified by Western blot analysis.

Production of microRNA

Human miRNA-34a (SEQ ID NO: 1; UGGCAGUGUC-UUAGCUGGUUGU) or miRNA-34c (SEQ ID NO: 2; AGGCAGUGUAGUUAGCUGAUUGC) was purchased from Thermo Fisher Scientific. $4 \times 10^5$ HGF-independent human gastric cancer SNU638 cells were seeded and transfected with 300 nM of miRNA-34a or miRNA-34c, and then the number of cells was counted using trypan blue exclusion method for 0, 1, 2 and 3 days.

Determination of Cell Growth $4 \times 10^5$ HGF-independent human gastric cancer SNU638 cells or $3 \times 10^5$ MKN45 cells were transfected with 300 nM of miRNA-34a (SEQ ID NO: 1) or miRNA-34c (SEQ ID NO: 2), and then the number of cells was counted using trypan blue exclusion method for 0, 1, 2 and 3 days.

Production of Antagomir

Antagomirs of human miRNA-34a and miRNA-34c were purchased from Thermo Fisher Scientific. $4 \times 10^5$ HGF-independent human gastric cancer SNU638 cells or $3 \times 10^5$ MKN45 cells were seeded and transfected with 300 nM of miRNA-34a or miRNA-34c, and then the number of cells was counted using a trypan blue exclusion method for 0, 1, 2 and 3 days.

Example 1

Identification of IGSF1 as a Marker for Induction of HGF-Independent MET Phosphorylation To identify a marker for the induction of HGF-independent MET phosphorylation, the present inventors induced the HGF-independent MET phosphorylation by overexpressing the MET wild-type DNA in HGF-negative human gastric cancer cell line AGS (FIG. 1A, left graph). We performed immunoprecipitation using p-MET antibody and then silver staining was performed to identify the protein binding to MET (FIG. 1A, right gel image).

Moreover, MALDI-TOF analysis was performed on the product to identify the protein binding to MET.

As a result, as shown in FIG. 1B, immunoglobulin superfamily member 1 (IGSF1) was identified as a marker for the induction of HGF-independent MET phosphorylation.

Example 2

Determination of Correlation Between the Expression of IGSF1 as a Marker for the Induction of HGF-Independent MET Phosphorylation and the Phosphorylation of MET 2-1. Analysis of the Expression of IGSF1 as a Marker for the Induction of HGF-Independent MET Phosphorylation and the Phosphorylation of MET in Human Gastric Cancer Cell Lines To determine the correlation between the expression of IGSF1 as a marker for the induction of HGF-independent MET phosphorylation and the phosphorylation of MET, the present inventors performed Western blot analysis using IGSF1 and pMET (phosphorylated active MET) antibodies in a total of 8 types of gastric cancer cell lines.

Figure 2A:
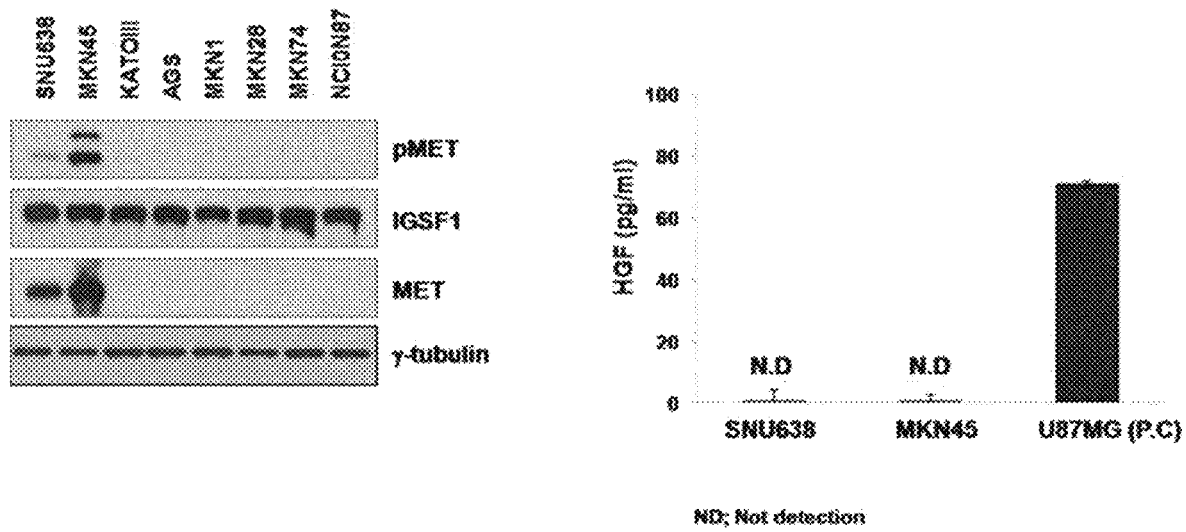
FIG. 2A shows the results of the analysis of correlation between the expression of IGSF1 as a marker for the induction of HGF-independent MET phosphorylation and the phosphorylation of MET in human gastric cancer cell lines. The left panel shows the results of western blot analysis performed using IGSF1 and pMET antibodies in 8 types of gastric cancer cell lines. The right panel shows that as a result of determining the HGF expression of SNU638 and MKN45, HGF was not detected as compared with the positive control U87MG cell line.

As a result, as shown in FIG. 2A (left), when MET and IGSF1 were co-expressed in human gastric cancer cell lines SNU638 and MKN45, the phosphorylation MET was observed.

Moreover, as a result of determining the HGF expression of SNU638 and MKN45, HGF was not detected as compared with the positive control U87MG cell line, as shown in FIG. 2A (right).

Therefore, it could be seen that the phosphorylation of MET was induced only in the case of HGF-negative (independent) and when MET and IGSF1 were co-expressed.

2-2. Analysis of Correlation Between the Expression of IGSF1 as a Marker for the Induction of HGF-Independent MET Phosphorylation and the Phosphorylation of MET in Human Lung Cancer Cell Lines To analyze the correlation between the expression of IGSF1 as a marker for the induction of HGF-independent MET phosphorylation and the phosphorylation of MET in human lung cancer cell lines, the present inventors performed Western blot analysis using IGSF1 and pMET (phosphorylated active MET) antibodies in a total of 9 types of lung cancer cell lines.

Figure 2B:
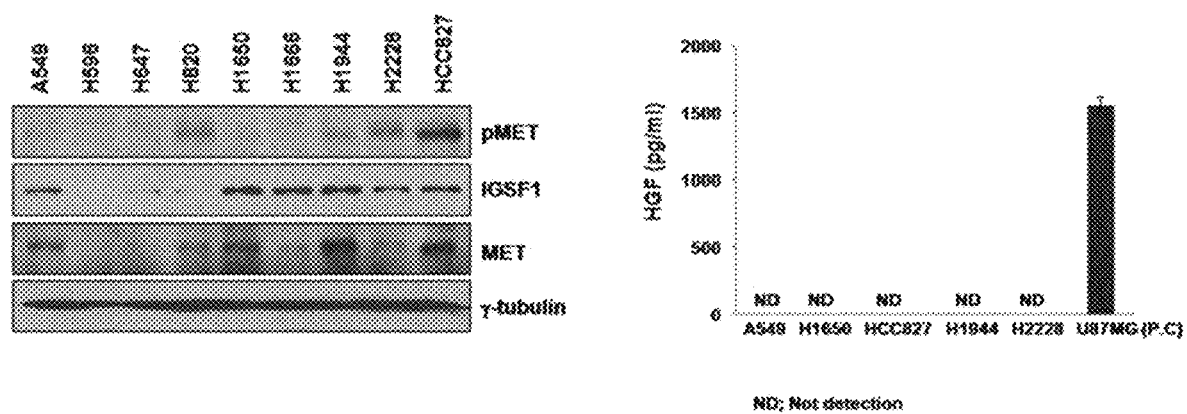
FIG. 2B shows the results of the analysis of correlation between the expression of IGSF1 as a marker for the induction of HGF-independent MET phosphorylation and the phosphorylation of MET in human lung cancer cell lines. Furthermore, the results of western blot analysis performed using IGSF1 and pMET antibodies in 9 types of lung cancer cell lines are shown. The left panel indicates that the phosphorylation of MET was observed when MET and IGSF1 were co-expressed in human lung cancer cell lines H1944, H2228 and HCC827. The right panel shows that HGF was not detected as compared with the positive control U87MG cell line.

As a result, as shown in FIG. 2B (left), the phosphorylation of MET was observed when MET and IGSF1 were co-expressed in human lung cancer cell lines H1944, H2228 and HCC827.

Moreover, as a result of determining the HGF expression of H1944, H2228 and HCC827, HGF was not detected as compared with the positive control U87MG cell line, as shown in FIG. 2B (right).

Therefore, it could be seen that the phosphorylation of MET was induced only in the case of HGF-negative (independent) and when MET and IGSF1 were co-expressed.

2-3. Determination of Binding Between IGSF1 as a Marker for the Induction of HGF-Independent MET Phosphorylation and the MET Protein in Human Gastric Cancer Cell Lines To analyze the binding between IGSF1 as a marker for the induction of HGF-independent MET phosphorylation and the MET protein in human gastric cancer cell lines, the present inventors overexpressed MET and IGSF1 in human gastric cancer cell line AGS, performed immunoprecipitation using p-MET antibody, and then determined the binding with IGSF1 by Western blot analysis.

Figure 2C:
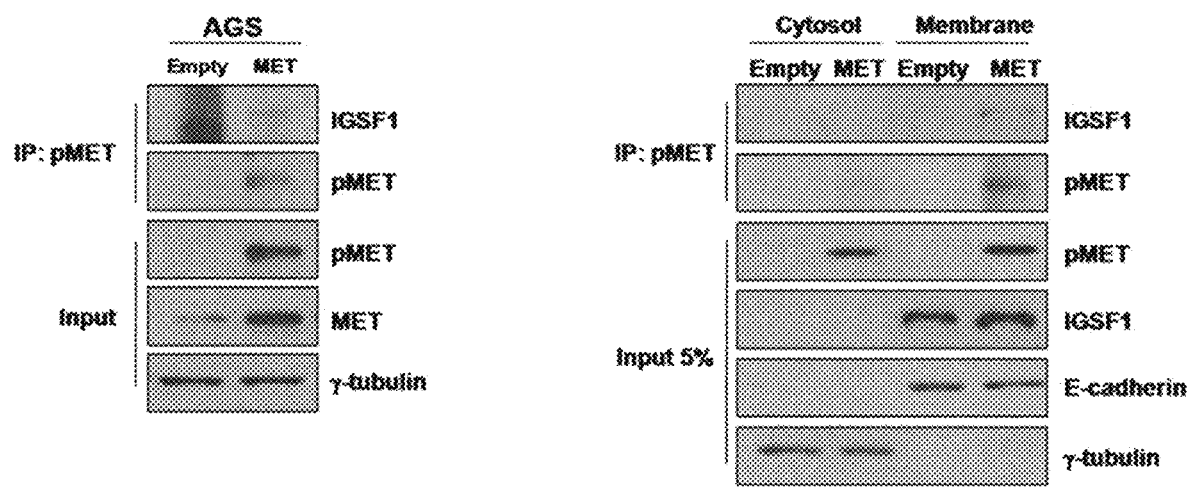
FIG. 2C shows the results of the analysis of binding between IGSF1 as a marker for the induction of HGF-independent MET phosphorylation and the MET protein in human gastric cancer cell lines. Furthermore, the results of binding between IGSF1 and MET determined by western blot analysis after overexpressing MET and IGSF1 in gastric cancer cell line AGS, followed by immunoprecipitation using p-MET antibody are shown. The left panel shows that when MET was overexpressed in HGF-negative human gastric cancer cell line AGS, it was found that MET bound to IGSF1. The right panel shows that when the cytosol and membrane of HGF-negative human gastric cancer cell line AGS with overexpressed MET were fractionated, it was found that MET bound to IGSF1 in the cell membrane.

As a result, as shown in FIG. 2C (left), when MET was overexpressed in HGF-negative human gastric cancer cell line AGS, it was found that MET bound to IGSF1.

Moreover, as shown in FIG. 2C (right), when the cytosol and membrane of HGF-negative human gastric cancer cell line AGS with overexpressed MET were fractionated, it was found that MET bound to IGSF1 in the cell membrane.

To determine where the two proteins bind to each other, the present inventors produced constructs with deletion of each domain of IGSF1 protein. Moreover, we produced constructs with deletion of extracellular domain and constructs with deletion of helical or cytoplasmic domain. MET WT and IGSF1 deletion constructs were transfected into 293T cells, and the positions where the proteins were bound were determined by immunoprecipitation.

Figure 2D:
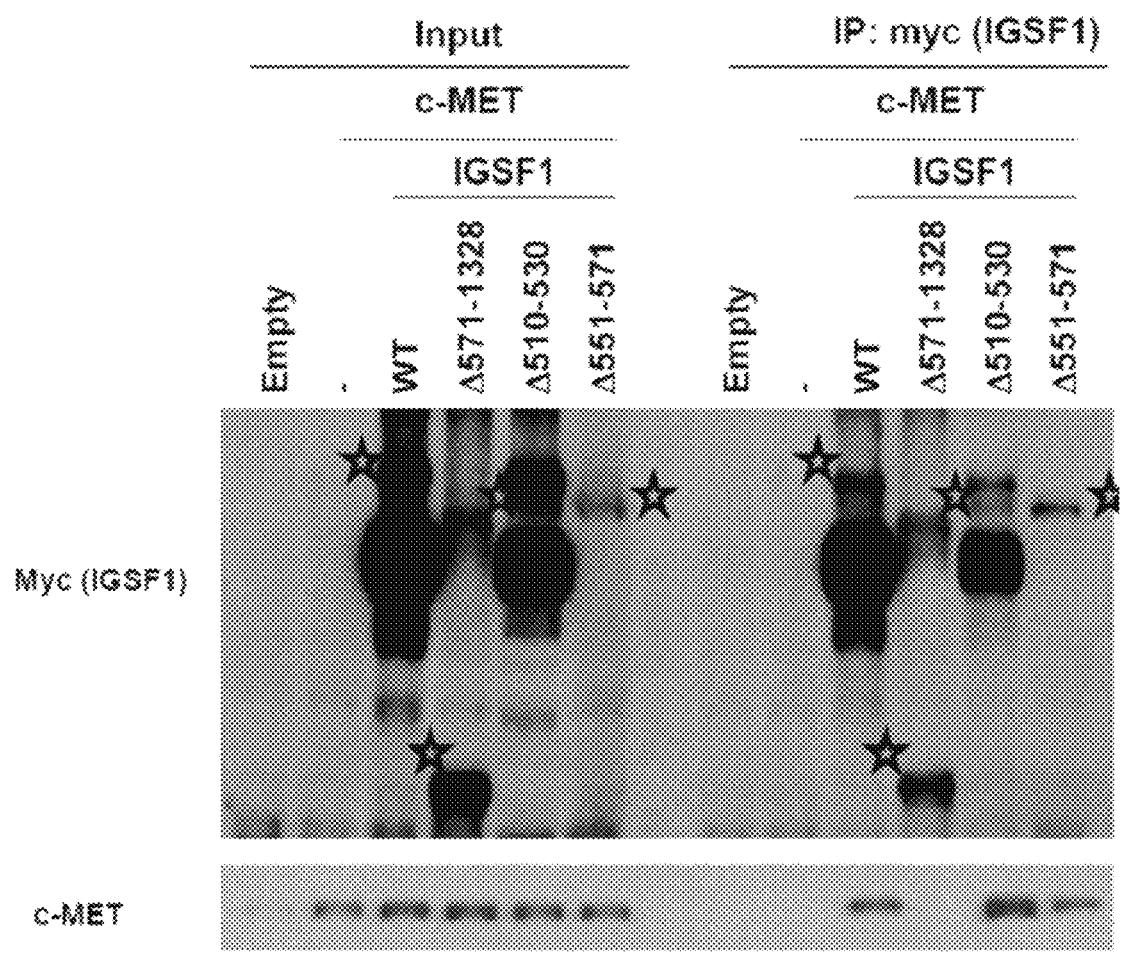
FIG. 2D shows the specific binding positions between IGSF1, a marker for the induction of HGF-independent MET phosphorylation, and MET in human gastric cancer cell lines, as well as the results of the analysis of binding between MET and IGSF1 proteins.

As a result, as shown in FIG. 2D, it was found that the protein did not bind in the 571-1328 deletions (extracellular domain), and thus it was found that the two proteins bound to each other at these positions. Moreover, it was found that WT MET and IGSF1 were bound to each other.

2-4. Changes in MET Phosphorylation by Inhibition of the Expression of IGSF1 as a Marker for the Induction of HGF-Independent MET Phosphorylation in Human Gastric Cancer Cell Lines and Lung Cancer Cell Line To analyze the changes in MET phosphorylation by inhibition of the expression of IGSF1 as a marker for the induction of HGF-independent MET phosphorylation in human gastric cancer cell line (AGS, MKN45, SNU638) and lung cancer cell line (HCC827), the present inventors inhibited the expression of IGSF1 or MET by the siRNA method and then determined the changes in phosphorylation of the MET protein by western blot analysis.

Figure 2E:
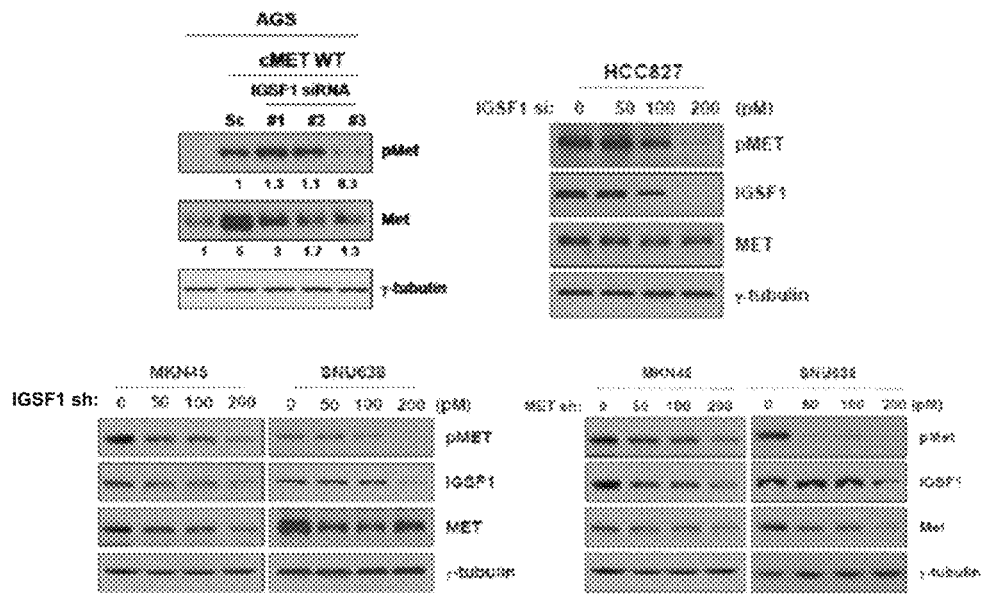
FIG. 2E shows the changes in phosphorylation of MET protein determined by western blot analysis after inhibiting the expression of IGSF1 or MET by siRNA method in human gastric cancer cell line (AGS) and lung cancer cell line (HCC827). To analyze the changes in MET phosphorylation by inhibition of the expression of IGSF1 as a marker for the induction of HGF-independent MET phosphorylation in human gastric cancer cell line (AGS (top, left panel), MKN45 (bottom panels), SNU638 (bottom panels)) and lung cancer cell line (HCC827 (top, right panel)), the expression of IGSF1 or MET was inhibited by the siRNA method and then the changes in phosphorylation of the MET protein were determined by western blot analysis.

As a result, as shown in FIG. 2E, the phosphorylation of MET decreased in an IGSF1 siRNA or shRNA concentration-dependent manner in human gastric cancer cell lines (AGS, MKN45, SNU638) and lung cancer cell line (HCC827). Moreover, the expression of IGSF1 decreased in an MET shRNA concentration-dependent manner.

2-5. Analysis of the Regulatory Mechanism Depending on Changes in Expression of IGSF1 or MET in Gastric Cancer Cell Lines The present inventors inhibited the expression of IGSF1 or MET by the shRNA method in human gastric cancer cell lines SNU638 and MKN45 and then determined the changes in expression of each gene by real-time PCR.

Figure 2F:
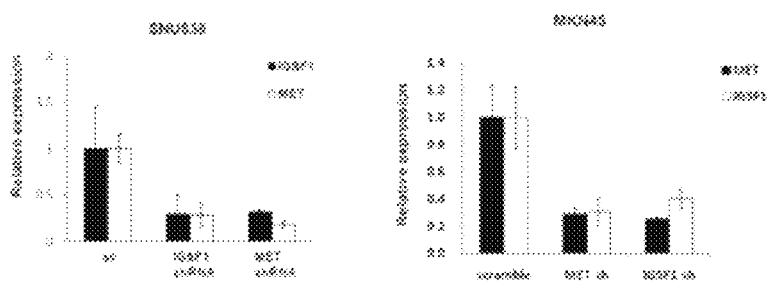
FIG. 2$f$ shows the results of the analysis of the regulatory mechanism depending on the changes in expression of IGSF1 or MET in gastric cancer cell lines.
Figure 2F:
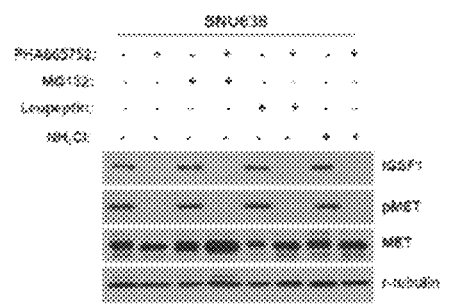

As a result, as shown in the upper panel of FIG. 2F, the expression of IGSF1 was decreased by the inhibition of expression of MET in both cell lines, and the expression of MET was decreased by the inhibition of expression of IGSF1. These results indicated that the expression was regulated at the RNA level.

Moreover, as shown in the lower panel of FIG. 2F, it was found that the expression of IGSF1 and MET were not regulated at the protein level in the gastric cancer cell lines. The results were obtained by Western blot analysis after treatment with an MET inhibitor, followed by treatment with the respective inhibitors to determine the regulation of the expression of IGSF1.

(PHA665752: c-MET inhibitor, MG132: proteasome inhibitor, Leupeptin & NH4Cl: lysosomal protease inhibitor)

Example 3

Inhibition of Cell Growth by Inhibition of IGSF1 as a Marker for the Induction of HGF-Independent MET Phosphorylation 3-1. Analysis of the Inhibition of Cell Growth by Inhibition of the Expression of IGSF1 as a Marker for the Induction of HGF-Independent MET Phosphorylation in Human Gastric Cancer Cell Lines The present inventors inhibited the expression of IGSF1 or MET by the shRNA method in human gastric cancer cell lines SNU638 and MKN45 and then determined the inhibition of cell growth.

Figure 3A:
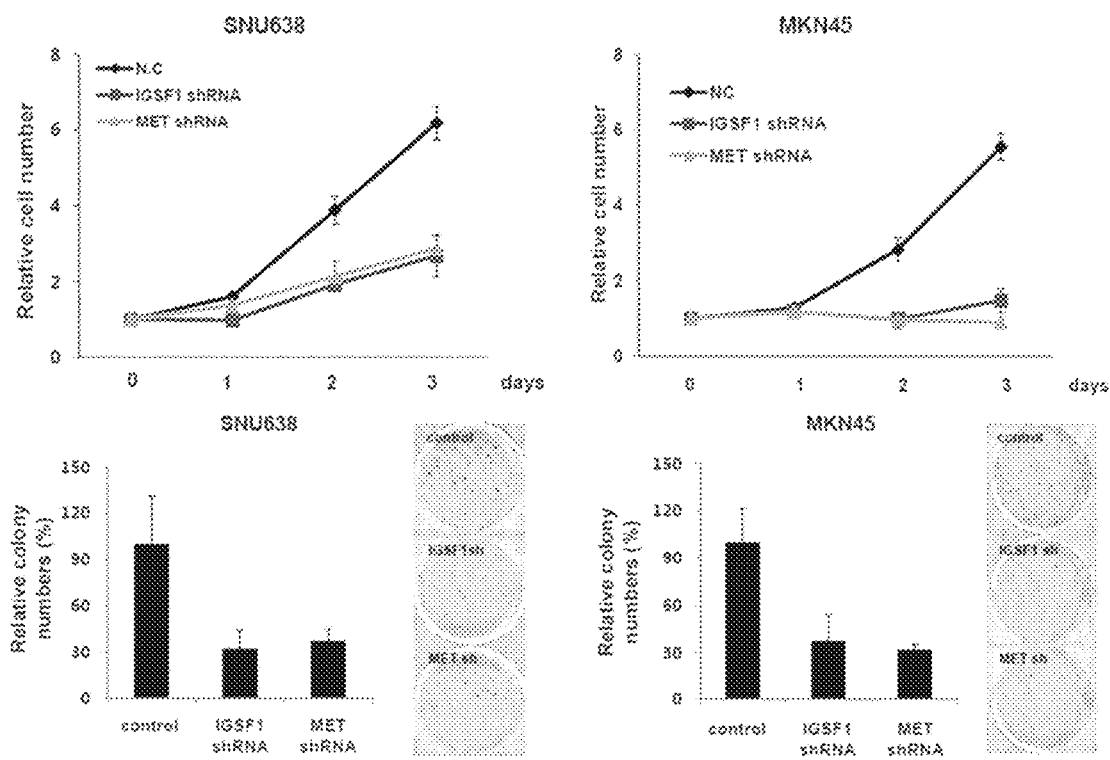
FIG. 3A shows the results of the inhibition of the growth of cancer cells by inhibition of the expression of IGSF1 as a marker for the induction of HGF-independent MET phosphorylation in human gastric cancer cell lines.

As a result, as shown in the upper panel of FIG. 3A, when the number of cells was counted for 3 days, it was found that the cell growth was inhibited by the inhibition of expression of MET or IGSF1.

Moreover, the expression of IGSF1 or MET in human gastric cancer cell lines SNU638 and MKN45 was inhibited, and then the degree of the inhibition of cell growth was determined by colony forming assay.

As a result, as shown in the lower panel of FIG. 3A, it was found that the number of colonies decreased by the inhibition of expression of IGSF1 or MET.

3-2. Analysis of the Inhibition of Cell Growth by Inhibition of the Expression of IGSF1 as a Marker for the Induction of HGF-Independent MET Phosphorylation in Human Lung Cancer Cell Lines The present inventors inhibited the expression of IGSF1 or the expression of MET by the shRNA method in human lung cancer cell lines HCC827 and HCC194 and then determined the inhibition of cell growth.

Figure 3B:
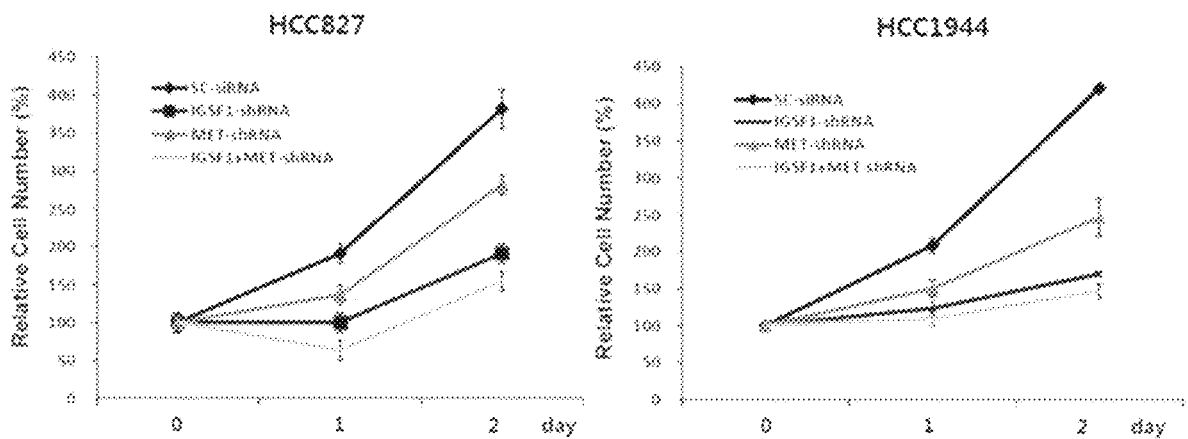
FIG. 3B shows the results of the inhibition of the growth of cancer cells by inhibition of the expression of IGSF1 as a marker for the induction of HGF-independent MET phosphorylation in human lung cancer cell lines.

As shown in FIG. 3B, as a result of counting the number of cells at 24 hours and 48 hours, it was found that the cell growth was inhibited in the group with the inhibition of expression of MET or IGSF1.

Example 4

Determination of the Inhibition of Invasion and Migration of Cancer Cells by Inhibition of the Expression of IGSF1 as a Marker for the Induction of HGF-Independent MET Phosphorylation 4-1. Analysis of the Inhibition of Invasion and Migration of Cancer Cells by Inhibition of the Expression of IGSF1 as a Marker for the Induction of HGF-Independent MET Phosphorylation in Human Gastric Cancer Cell Lines The present inventors inhibited the expression of IGSF1 by the siRNA method in human gastric cancer cell lines SNU638 and MKN45 and then analyzed the degree of the inhibition of invasion and migration by invasion chamber assay and wound healing assay.

Figure 4A:
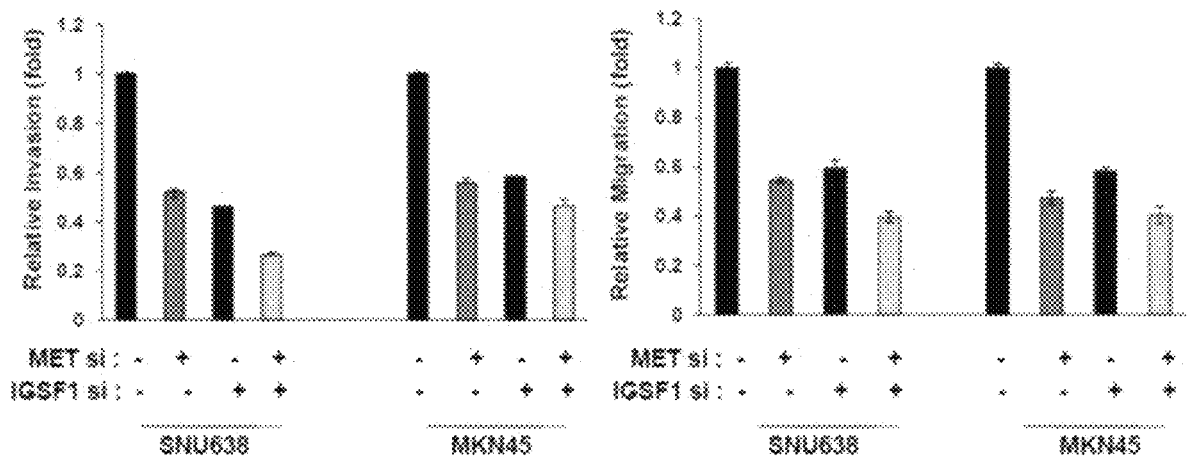
FIG. 4A shows the results of the inhibition of invasion and migration of cancer cells by inhibition of the expression of IGSF1 as a marker for the induction of HGF-independent MET phosphorylation in human gastric cancer cell lines.

As a result, as shown in FIG. 4A, it was observed that the cells inhibiting the expression of IGSF1 and the cells inhibiting the expression of MET similarly inhibited invasion and migration.

4-2. Analysis of the Inhibition of Invasion and Migration of Cancer Cells by Inhibition of the Expression of IGSF1 as a Marker for the Induction of HGF-Independent MET Phosphorylation in Human Lung Cancer Cell Lines The present inventors inhibited the expression of IGSF1 by the siRNA method in human lung cancer cell lines HCC827 and H1944 and then analyzed the degree of the inhibition of invasion and migration by invasion chamber assay and wound healing assay.

Figure 4B:
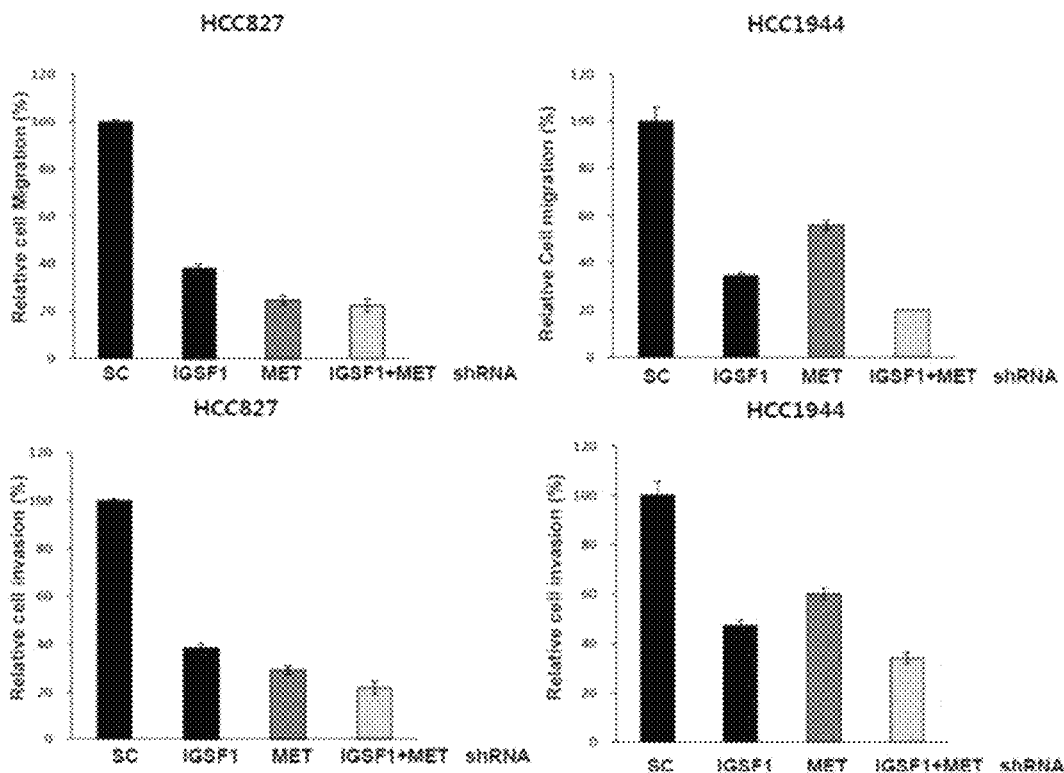
FIG. 4B shows the results of the inhibition of invasion of cancer cells by inhibition of the expression of IGSF1 as a marker for the induction of HGF-independent MET phosphorylation in human lung cancer cell lines.

As a result, as shown in FIG. 4B, it was observed that the inhibition of IGSF1 in HCC827 and H1944 decreased the invasion to 80% or less as compared with the control (sc). In the case of the MET inhibition, a similar pattern was observed.

Example 5

Figure 5A:
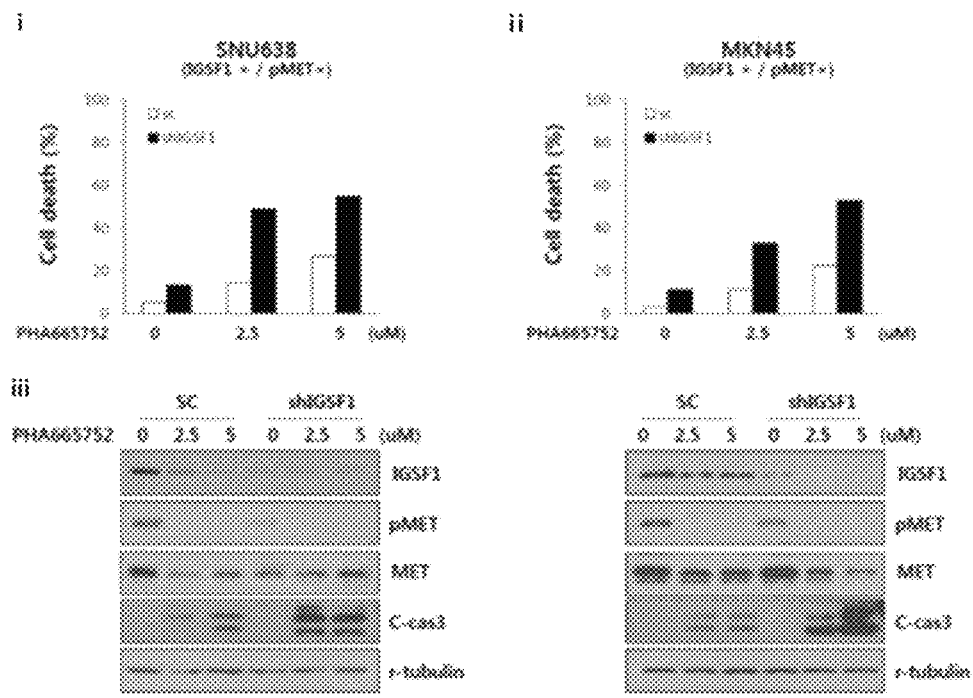
FIG. 5A shows the results of the comparative analysis of the efficacy of MET inhibitor depending on the presence or absence of IGSF1 expression in gastric cancer cell lines. Panel i shows the apoptosis induced by treatment of a MET inhibitor (PHA665752) at each concentration in SNU638 cell line, determined by trypan blue exclusion, and panel ii shows the results of the same experiment performed on MKN45 cell line. Panel iii shows the expression of cleaved caspase 3 (C-cas3) in cell lines (SNU638 and MKN45) increased by treatment of a MET inhibitor (PHA665752) at each concentration.
Figure 5B:
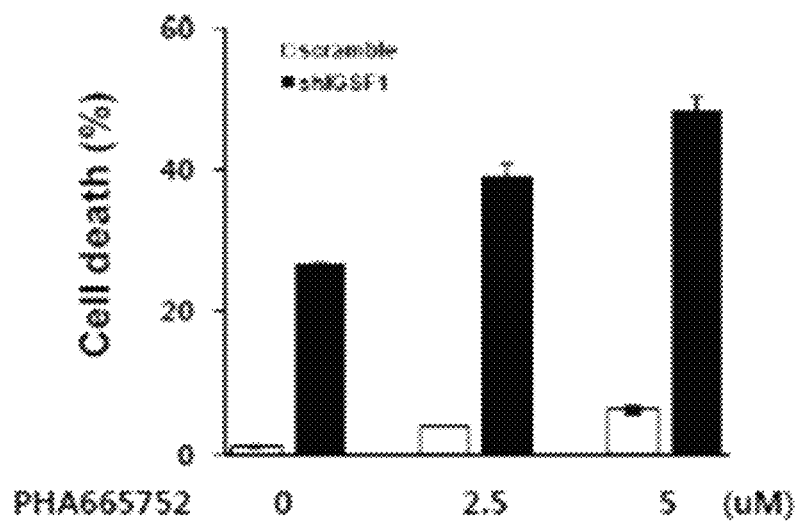
FIG. 5b shows the results of the comparative analysis of the efficacy of MET inhibitor depending on the presence or absence of IGSF1 expression in lung cancer cell line.

Analysis of the Effect of IGSF1 on the Use of an MET Inhibitor in Gastric Cancer and Lung Cancer Cell Lines 5-1. Comparative Analysis of the Efficacy of MET Inhibitor Depending on the Presence or Absence of IGSF1 Expression in Gastric Cancer Cell Lines The present inventors found that the inhibition of the expression of IGSF1 in the gastric cancer cell lines SNU638 and MKN45 increased the response to the MET inhibitor. As shown in FIG. 5A, the induction of apoptosis by treatment of an MET inhibitor, PHA665752, at each concentration was determined by trypan blue exclusion, proving that the expression of cleaved caspase 3 increased.

5-2. Comparative Analysis of the Efficacy of MET Inhibitor Depending on the Presence or Absence of IGSF1 Expression in Lung Cancer Cell Line The present inventors found that the inhibition of the expression of IGSF1 in lung cancer cell line HCC827 increased apoptosis and increased the response to the MET inhibitor.

Example 6

Simultaneous Inhibition of the Expression of IGSF1 as a Marker for the Induction of HGF-Independent MET Phosphorylation and the Expression of c-MET Using MicroRNA 6-1. Analysis of the Inhibition of IGSF1 and MET by miR-34a and miR-34c that Simultaneously Inhibit the Expression of IGSF1 as a Marker for the Induction of HGF-Independent MET Phosphorylation and the Expression of c-MET To analyze the degree of the inhibition by miR-34a and miR-34c that simultaneously inhibit the expression of IGSF1 as a marker for induction of HGF-independent MET phosphorylation and the expression of MET, the present inventors transfected the human 293 cell line with miR-34a or miR-34c using wild-type IGSF1, wild-type MET, and luciferase plasmids containing the mutated 3'UTR thereof.

Figure 6A:
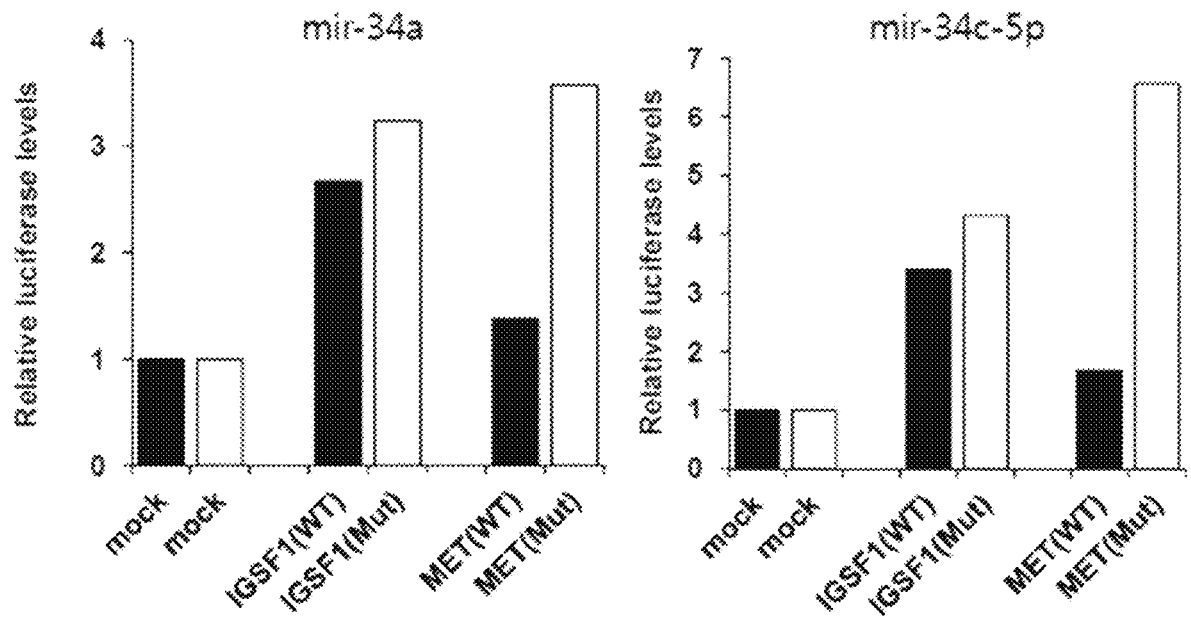
FIG. 6A shows the results of the simultaneous inhibition of IGSF1, a marker for induction of HGF-independent MET phosphorylation, and MET using microRNA.

As a result, as shown in FIG. 6A, miR-34a and miR-34c exhibited low luciferase activity in wild-type MET. That is, the luciferase activity of IGSF1 and MET by miR-34a and miR-34c was inhibited only in the wild type. It was found that miR-34a and miR-34c bound simultaneously to the 3'UTR region of MET and IGSF1 genes and simultaneously inhibit the expression of both genes.

6-2. Changes in Expression of IGSF1 and c-MET by miR-34a and miR-34c that Simultaneously Inhibit the Expression of IGSF1 as a Marker for Induction of HGF-Independent MET Phosphorylation and the Expression of c-MET To analyze the degree of the change in IGSF1 and MET by miR-34a and miR-34c that simultaneously inhibit the expression of IGSF1 as a marker for induction of HGF-independent MET phosphorylation and the expression of MET, the present inventors transfected human gastric cancer cell lines MKN45 and SNU638 with miR-34a or miR-34c and then determined the expression of MET and the expression of IGSF1 by real-time PCR.

Figure 6B:
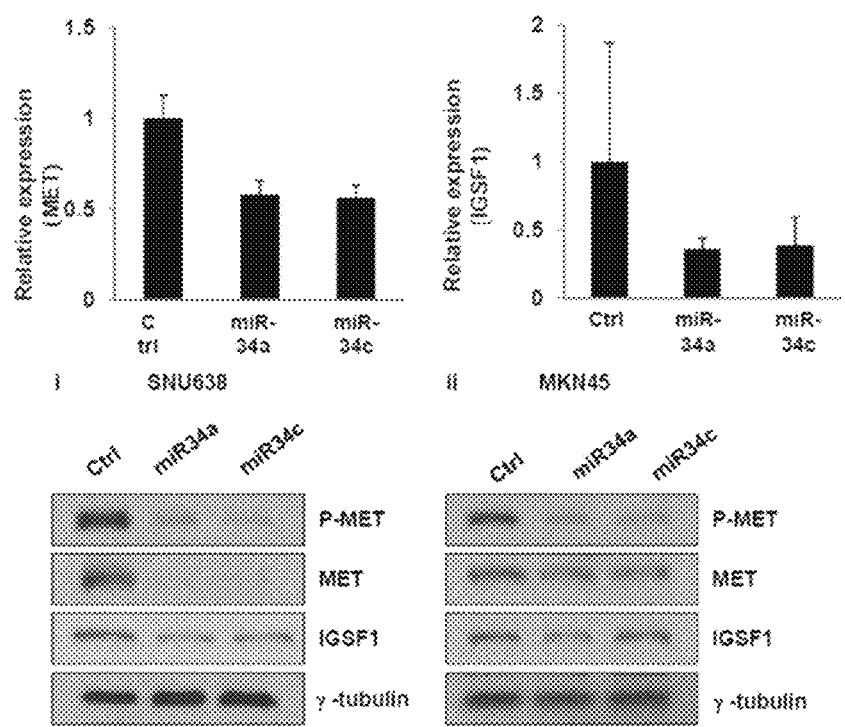
FIG. 6B shows the changes in expression of IGSF1 and MET by miR-34a and miR-34c that simultaneously inhibit the expression of IGSF1 as a marker for induction of HGF-independent MET phosphorylation and the expression of MET.

As a result, as shown in the upper panel of FIG. 6B, it was observed that the expression of IGSF1 as a marker for the induction of HGF-independent MET phosphorylation and the expression of MET were decreased by miR-34a or miR-34c in cell line SNU638.

Moreover, as shown in the lower panel of FIG. 6B, as a result of analyzing the expression of MET and IGSF1 after transfecting miR-34a or miR-34c into human gastric cancer cell lines MKN45 and SNU638, it was observed that the expression of IGSF1 as a marker for the induction of HGF-independent MET phosphorylation and the expression of c-MET were inhibited by miR-34a or miR-34c.

6-3. Analysis of Cell Growth by miR-34a and miR-34c that Simultaneously Inhibit the Expression of IGSF1 as a Marker for Induction of HGF-Independent MET Phosphorylation and the Expression of c-MET To analyze the cell growth by miR-34a and miR-34c that simultaneously inhibit the expression of IGSF1 as a marker for induction of HGF-independent MET phosphorylation and the expression of MET, the present inventors transfected human gastric cancer cell line SNU638 with miR-34a or miR-34c and then determined the growth of cancer cells.

Figure 6C:
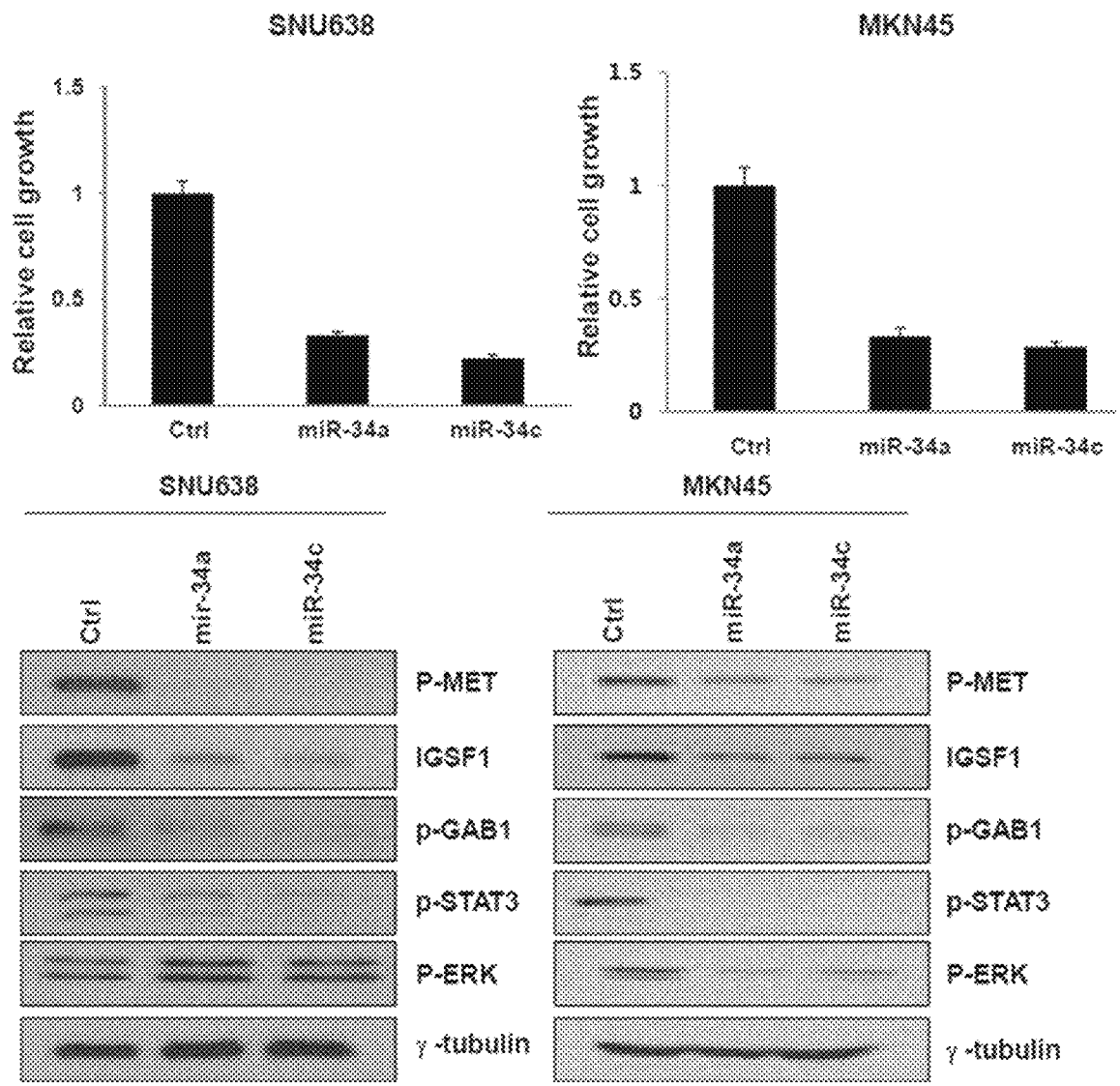
FIG. 6C shows the results of the cell growth assay by miR-34a and miR-34c that simultaneously inhibit the expression of IGSF1 as a marker for induction of HGF-independent MET phosphorylation and the expression of MET.

As a result, as shown in the upper panel of FIG. 6C, it was observed that the growth of cancer cells was significantly inhibited by miR-34a or miR-34c as compared with the control group.

Moreover, as shown in the lower panel of FIG. 6C, it was found that the transfection of the human gastric cancer cell line with miR-34a or miR-34c decreased the expression of the relevant signaling pathway.

6-4. Analysis of the Inhibition of Cell Invasion and Migration by miR-34a and miR-34c that Simultaneously Inhibit the Expression of IGSF1 as a Marker for Induction of HGF-Independent MET Phosphorylation and the Expression of c-MET As shown in the upper panel of FIG. 6D, the present inventors found that the transfection of gastric cancer cell lines SNU638 and MKN45 with mir-34a or mir-34c inhibited the cell migration.

Figure 6D:
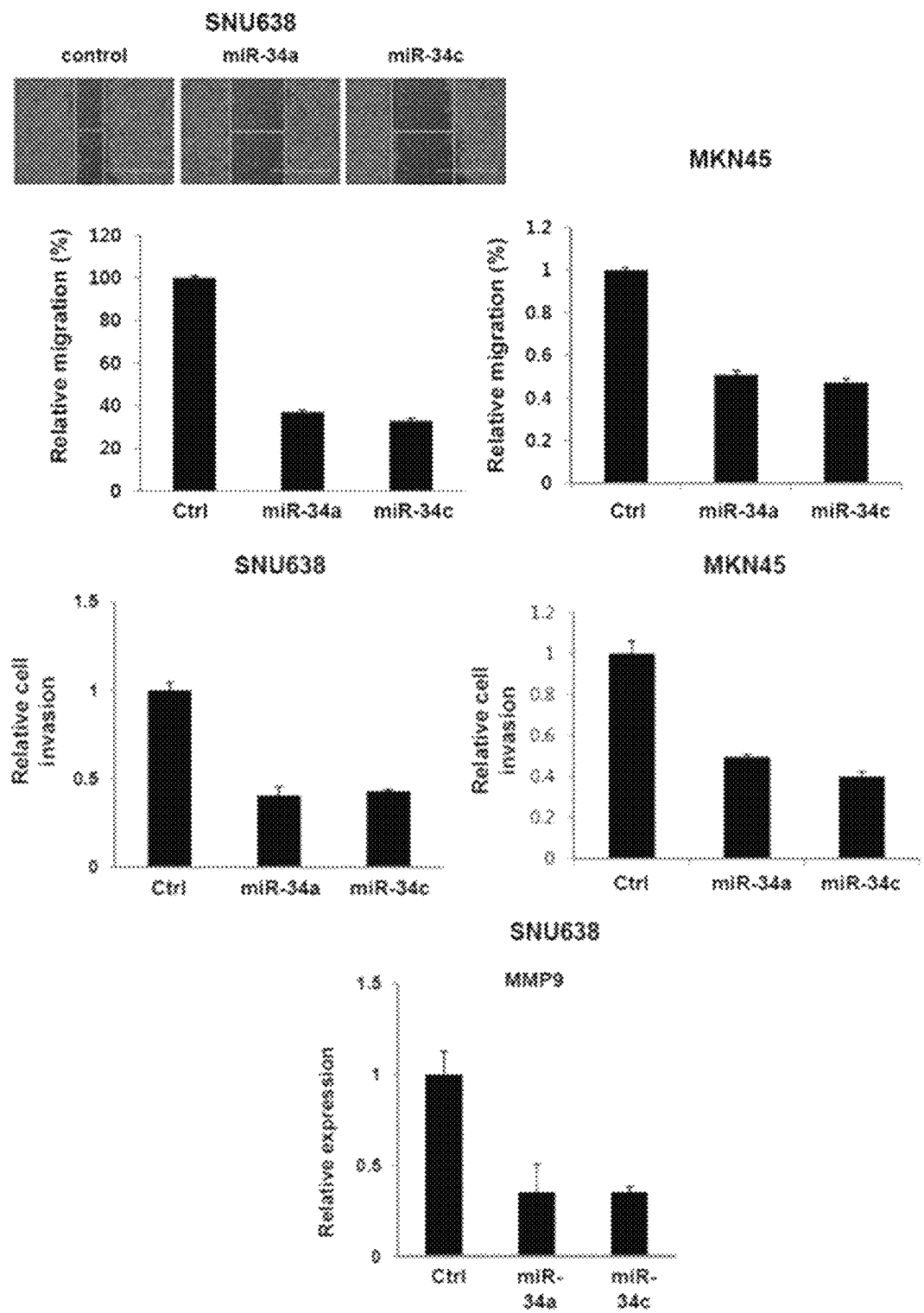
FIG. 6D shows the results of the inhibition of cell invasion and migration by miR-34a and miR-34c that simultaneously inhibit the expression of IGSF1 as a marker for induction of HGF-independent MET phosphorylation and the expression of MET.

Moreover, as shown in the middle panel of FIG. 6D, it was found that the transfection of the gastric cancer cell line with mir-34a or mir-34c inhibited the invasion of cells by about 50%.

Furthermore, as shown in the lower panel of FIG. 6D, the transfection of gastric cancer cell line SNU638 with mir-34a or mir-34c inhibited the migration of cells and decreased the expression of MMP9.

6-5. Recovery of Inhibition of IGSF1 and MET by mir-34a and mir-34c Using Antagomir As shown in the upper panel of FIG. 6E, the present inventors found that the transfection of gastric cancer cell line SNU638 with anti-mir-34a or anti-mir-34c recovered the expression of MET and IGSF1 that was inhibited by mir-34a or mir-34c at the RNA level (left) and the protein level (right).

Figure 6E:
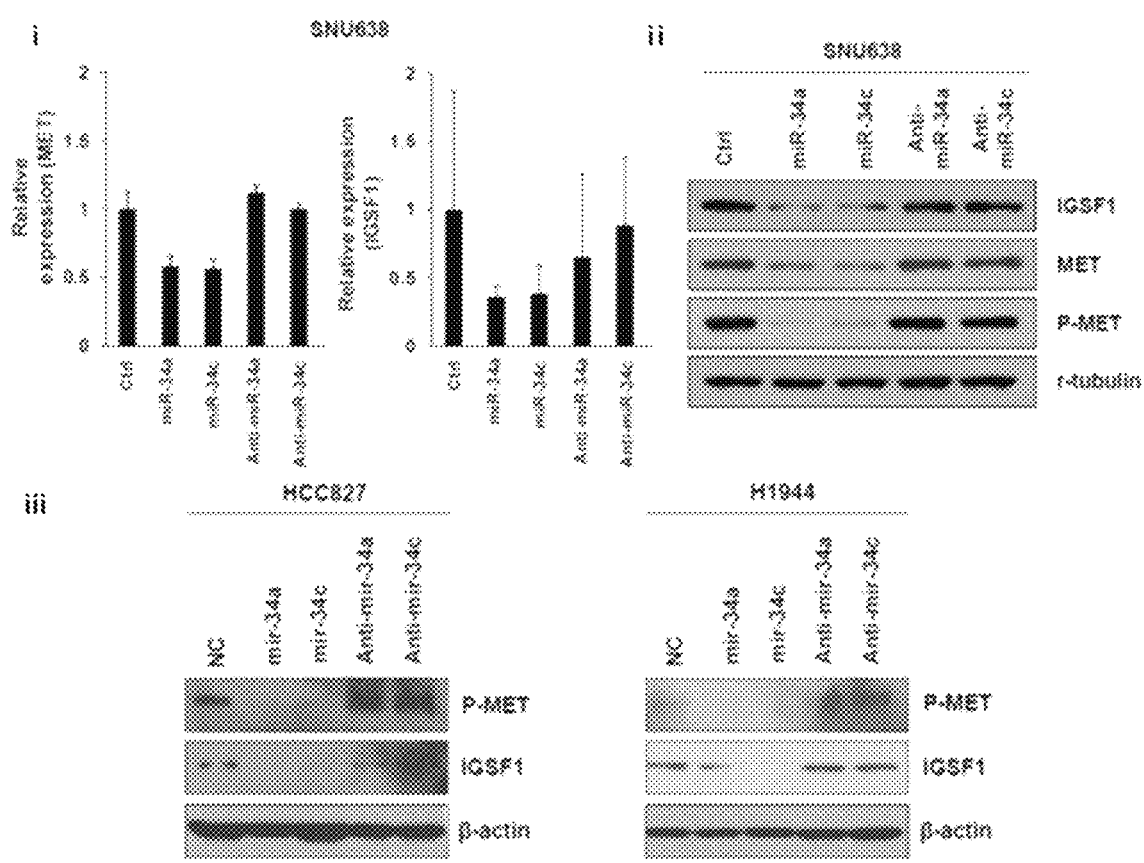
FIG. 6E shows the recovery of the expression of IGSF1 and MET inhibited by mir-34a and mir-34c using antagomir. Panel i shows the expression of MET and IGSF1, which was inhibited by miR-34a or miR-34c, recovered by transfection of gastric cancer cell line SNU638 with anti-miR-34a or anti-miR-34c, determined at the RNA level. Panel ii shows the results determined at the protein level. Panel iii shows decreased expression of pMET and IGSF1 and recovered expression of proteins, which was inhibited by anti-miR-34a and anti-miR-34c, by transfection of lung cancer cell lines HCC827 and H1944 with miR-34a or miR-34c.

Moreover, as shown in the lower panel of FIG. 6E, we found that the transfection of lung cancer cell lines HCC827 and H1944 with mir-34a or mir-34c decreased the expression of pMET and IGSF1 and recovered the expression of proteins that was inhibited by anti-mir-34a and anti-mir-34c.

Figure 6F:
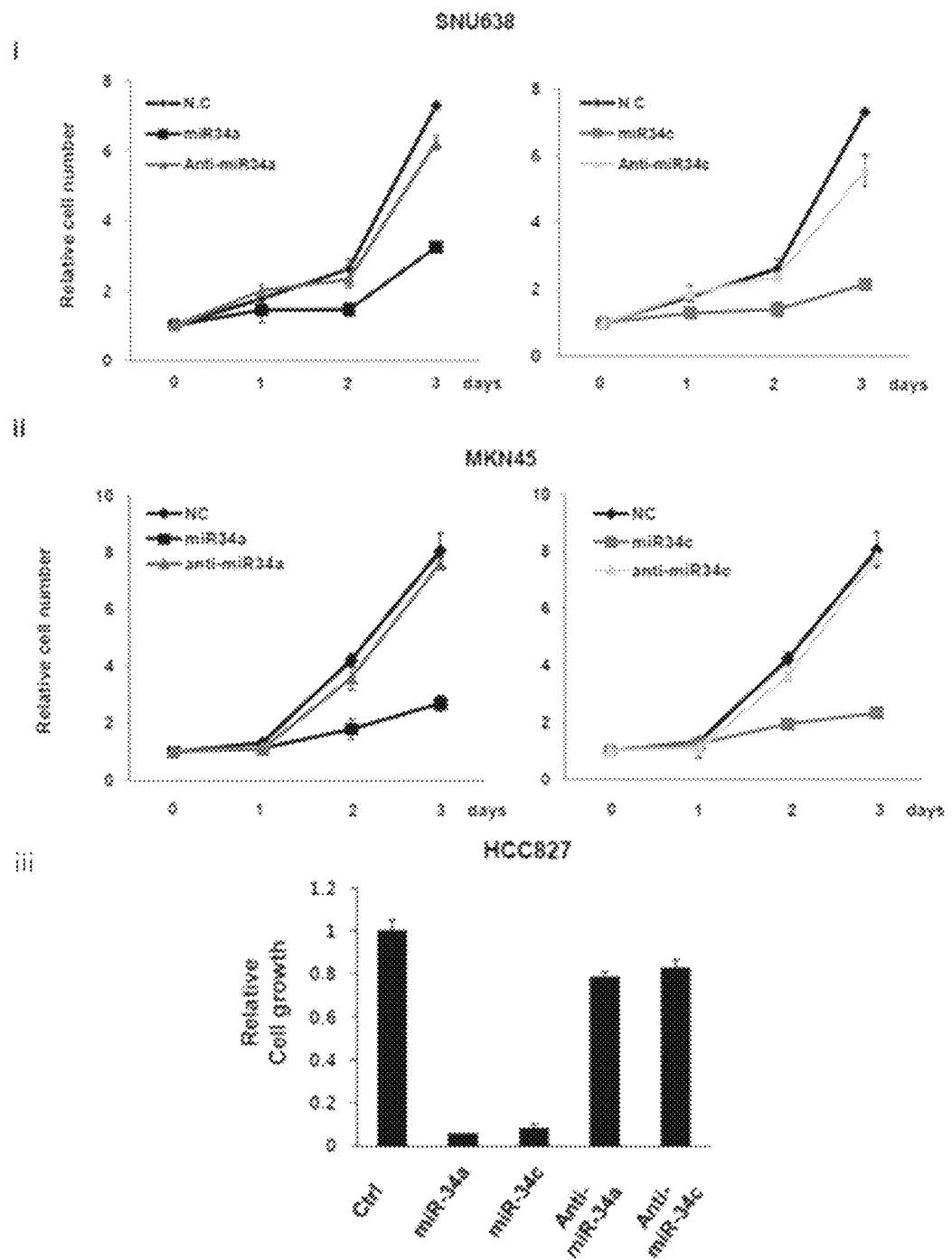
FIG. 6F shows the cell growth recovered by transfection of gastric cancer cell lines SNU638 and MKN45 with anti-miR-34a or anti-miR-34c (panels i and ii). Panel iii shows the results determined by the same experiment performed on lung cancer cell line (HCC827).

Meanwhile, as shown in the upper panel of FIG. 6F, the cell growth recovered by anti-mir-34a or anti-mir-34c in gastric cancer cell lines SNU638 and MKN45 was compared with the results of mir-34a and mir-34c.

Further, as shown in the lower panel of FIG. 6F, the recovery of the cell growth was found from the same experiment on the lung cancer cell line.

Figure 6G:
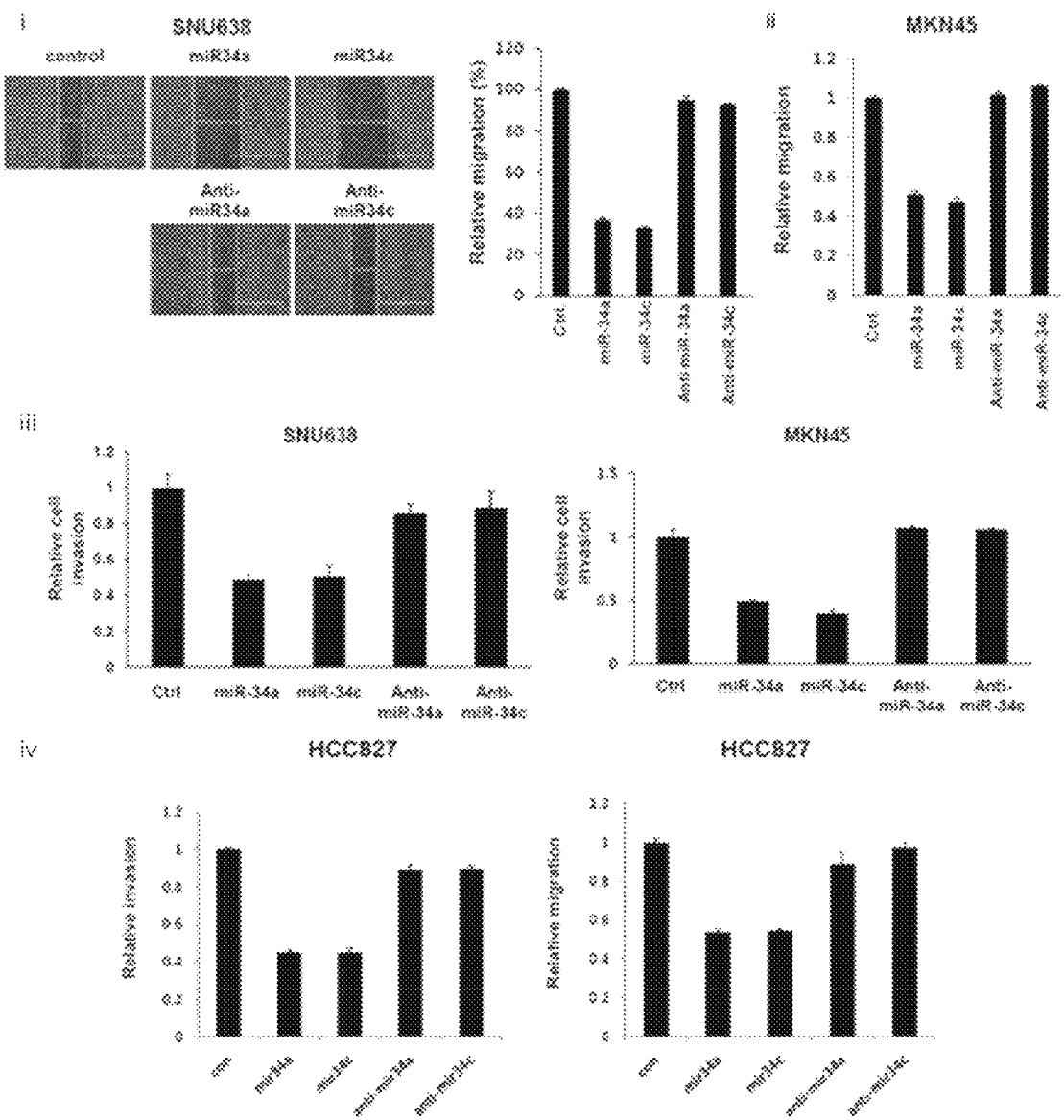
FIG. 6G shows the migration of cells recovered by transfection of gastric cancer cell lines SNU638 and MKN45 with anti-miR-34a or anti-miR-34c (panels i and ii). Panel iii shows the invasion of cells was recovered by transfection of gastric cancer cell lines SNU638 and MKN45 with anti-miR-34a or anti-miR-34c. Panel iv shows recovered invasion and migration of cells determined by the same experiment performed on lung cancer cell line (HCC827).

Meanwhile, as shown in the upper panel of FIG. 6G, it was found that the migration of cells was recovered by anti-mir-34a or anti-mir-34c in the gastric cancer cell line.

In addition, as shown in the middle panel of FIG. 6G, it was found that the invasion of cells was recovered by anti-mir34a or anti-mir-34c in the gastric cancer cell line.

Additionally, as shown in the bottom panel of FIG. 6G, it was found that the invasion and migration of cells were recovered by anti-mir-34a or anti-mir-34c in the lung cancer cell line (HCC827).

Therefore, IGSF1, which induces HGF-independent MET phosphorylation, and MET show the potential as biomarkers for predicting susceptibility to MET inhibitors.

Example 7

Determination of the Activity of MET and the Expression Levels of IGSF1 and HGF in Tissues of Gastric Cancer Patients In order to determine the activity of MET and the expression levels of IGSF1 and HGF in tissues of gastric cancer patients, TMA slides were purchased from US Biomax and immunochemical staining was performed.

Figure 7:
FIG. 7 shows the ratio of the activated expression of IGSF1, a marker for induction of HGF-independent MET phosphorylation, MET and in tissues of gastric cancer patients, as well as the representative patient's samples.

As a result, as shown in the upper panel of FIG. 7, the activity of MET was observed in tissue microarray (TMA) tissues of gastric cancer patients with the expression of IGSF1, and the ratio of HGF not expressed was about 30%.

The invention claimed is:

1. A method for treating gastric cancer cells or lung cancer cells, wherein said cells have been identified as having expression of the human immunoglobulin superfamily member 1 (IGSF1) gene and wherein said cells have been identified as having hepatocyte growth factor (HGF)-independent MET activation, the method comprising co-administering (a) an agent targeted to IGSF1 for inhibiting the expression of the IGSF1 gene or the expression or activity of its protein; and (b) an agent targeted to MET.

2. The method of claim 1, wherein the agent targeted to MET is a selective small molecule MET kinase inhibitor.

3. The method of claim 1, wherein the agent targeted to IGSF1 comprises at least one selected from the group consisting of small interfering RNA (siRNA) and short hairpin RNA (shRNA).

4. The method of claim 1, wherein the agent targeted to IGSF1 is selected from the group consisting of IGSF1 siRNA comprising the nucleotide sequence of SEQ ID NO:3, IGSF1 siRNA comprising the nucleotide sequence of SEQ ID NO:4, and IGSF1 shRNA comprising the nucleotide sequence of SEQ ID NO:6, wherein the agent targeted to MET is selected from the group consisting of MET siRNA comprising the nucleotide sequence of SEQ ID NO:5, and MET shRNA comprising the nucleotide sequence of SEQ ID NO: 7.

5. The method of claim 1, wherein the agent targeted to MET comprises an inhibitor for inhibiting the expression of MET gene or the expression or activity of its protein as an active ingredient.

6. A method for treating gastric cancer cells or lung cancer cells in a patient, the method comprising:

obtaining or having obtained a biological sample from the patient;

detecting or having detected the presence or absence of expression of at least the human immunoglobulin superfamily member 1 (IGSF1) gene in the biological sample;

identifying or having identified whether MET is activated in a hepatocyte growth factor (HGF)-independent manner or -dependent manner in the biological sample; and if the IGSF1 gene is expressed and MET is activated in an HGF-independent manner, then co-administering to said patient a therapeutically effective amount of an agent targeted to IGSF1 and an agent targeted to MET.

7. The method of claim 6, wherein the agent targeted to MET is a selective small molecule MET kinase inhibitor.

8. The method of claim 6, wherein the agent targeted to IGSF1 comprises at least one selected from the group consisting of small interfering RNA (siRNA) and short hairpin RNA (shRNA).

9. The method of claim 6, wherein the agent targeted to IGSF1 is selected from the group consisting of IGSF1 siRNA comprising the nucleotide sequence of SEQ ID NO:3, IGSF1 siRNA comprising the nucleotide sequence of SEQ ID NO:4, and IGSF1 shRNA comprising the nucleotide sequence of SEQ ID NO:6, wherein the agent targeted to MET is selected from the group consisting of MET siRNA comprising the nucleotide sequence of SEQ ID NO:5, and MET shRNA comprising the nucleotide sequence of SEQ ID NO: 7.

10. The method of claim 6, wherein the agent targeted to MET comprises an inhibitor for inhibiting the expression of MET gene or the expression or activity of its protein as an active ingredient.

11. A method for treating gastric cancer cells or lung cancer cells in a patient, the method comprising:

identifying the patient as having expression of an immunoglobulin superfamily member 1 (IGSF1) gene and having MET activated in an HGF-independent manner, and co-administering to said patient a therapeutically effective amount of an agent targeted to IGSF1 and an agent targeted to MET.

12. The method of claim 11, wherein the agent targeted to MET is a selective small molecule MET kinase inhibitor.

13. The method of claim 11, wherein the agent targeted to IGSF1 comprises at least one selected from the group consisting of small interfering RNA (siRNA) and short hairpin RNA (shRNA).

14. The method of claim 11, wherein the agent targeted to IGSF1 is selected from the group consisting of IGSF1 siRNA comprising the nucleotide sequence of SEQ ID NO:3, IGSF1 siRNA comprising the nucleotide sequence of SEQ ID NO:4, and IGSF1 shRNA comprising the nucleotide sequence of SEQ ID NO:6, wherein the agent targeted to MET is selected from the group consisting of MET siRNA comprising the nucleotide sequence of SEQ ID NO:5, and MET shRNA comprising the nucleotide sequence of SEQ ID NO: 7.

15. The method of claim 11, wherein the agent targeted to MET comprises an inhibitor for inhibiting the expression of MET gene or the expression or activity of its protein as an active ingredient.

* * * * *

SEQUENCE LISTING

```
<160> NUMBER OF SEQ ID NOS: 7

<210> SEQ ID NO 1
<211> LENGTH: 22
<212> TYPE: RNA
<213> ORGANISM: Artificial Sequence
<220> FEATURE:
<223> OTHER INFORMATION: miRNA

<400> SEQUENCE: 1
uggcaguguc uuagcugguu gu                                                  22

<210> SEQ ID NO 2
<211> LENGTH: 23
<212> TYPE: RNA
<213> ORGANISM: Artificial Sequence
<220> FEATURE:
<223> OTHER INFORMATION: miRNA

<400> SEQUENCE: 2
aggcagugua guuagcugau ugc                                                 23

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
gcaggucuuu accggugcu                                                      19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
ggugcugcua cuggaagga                                                      19

<210> SEQ ID NO 5
```

```
<211> LENGTH: 21
<212> TYPE: RNA
<213> ORGANISM: Artificial Sequence
<220> FEATURE:
<223> OTHER INFORMATION: siRNA

<400> SEQUENCE: 5
aaagauaaac cucucauaau g                                              21

<210> SEQ ID NO 6
<211> LENGTH: 44
<212> TYPE: RNA
<213> ORGANISM: Artificial Sequence
<220> FEATURE:
<223> OTHER INFORMATION: shRNA

<400> SEQUENCE: 6
caaagaugga agugaaauau cucuauuuca cuuccaucuu uguu                     44

<210> SEQ ID NO 7
<211> LENGTH: 44
<212> TYPE: RNA
<213> ORGANISM: Artificial Sequence
<220> FEATURE:
<223> OTHER INFORMATION: shRNA

<400> SEQUENCE: 7
gccagccuga augaugacau cucugucauc auucaggcug gcuu                     44
```